US005851794A

United States Patent [19]
Guss et al.

[11] Patent Number: 5,851,794
[45] Date of Patent: Dec. 22, 1998

[54] COLLAGEN BINDING PROTEIN AS WELL AS ITS PREPARATION

[75] Inventors: Bengt Guss, Uppsala, Sweden; Magnus Höök, Birmingham, Ala.; Hans Jönsson; Martin Lindberg, both of Uppsala, Sweden; Joseph Patti, Birmingham, Ala.; Christer Signäs, Uppsala, Sweden; Lech Switalski, Birmingham, Ala.

[73] Assignee: Alfa Laval AB, Tumba, Sweden

[21] Appl. No.: 447,031

[22] Filed: May 22, 1995

Related U.S. Application Data

[63] Continuation of Ser. No. 861,804, Aug. 21, 1992, abandoned.

[30] Foreign Application Priority Data

Oct. 22, 1990 [SE] Sweden ................................ 9003374-7

[51] Int. Cl.[6] .............................. C12P 21/06; C12N 1/20; C12N 15/09; C07H 21/04

[52] U.S. Cl. ................ 435/69.1; 435/252.3; 435/252.33; 435/320.1; 536/23.7

[58] Field of Search ................................ 435/69.1, 252.3, 435/252.33, 320.1; 530/350; 536/23.7

[56] References Cited

U.S. PATENT DOCUMENTS

| | | | |
|---|---|---|---|
| 5,175,096 | 12/1992 | Höök et al. | 435/69.1 |
| 5,189,015 | 2/1993 | Hook et al. | 424/243.1 |

OTHER PUBLICATIONS

Patti et al., J. Biol. Chem. 267: 4766–4772 (1992).

Patti et al., J. Biol. Chem. 269: 11672 (1994).

Switalski et al., J. Biol. Chem. 264: 21080–21086 (1989).

Hunkapiller et al., Meth. Enzymol. 91: 227–236 (1983).

Lathe, J. Mol. Biol. 183: 1–12 (1985).

Ohtsuka et al., J. Biol. Chem. 260: 2605–2608 (1985).

Genbank Accession Number M81736.

*Primary Examiner*—Robert A. Wax
*Assistant Examiner*—Elizabeth Slobodyansky
*Attorney, Agent, or Firm*—Burns, Doane, Swecker & Mathis

[57] ABSTRACT

The present invention relates to a new recombinant DNA-molecule comprising a nucleotide sequence from *S. aureus* coding for a protein, or polypeptide, having collagen binding properties.

9 Claims, 14 Drawing Sheets

```
    Part of the
    vector<--|--> 5' end of insert in p16
    MCS      |
    GGATCCCCAATTCTTTTAAAACTAGAAATTCACCCATTTTTCTTGATGATTCGTCTTTTG
1   ---------+---------+---------+---------+---------+---------+   60

    GTTTCGAACCAAATGATTCAGAAAGTGATTTGATAATTGGGAACATGATTCCACCAGCAC
61  ---------+---------+---------+---------+---------+---------+   120

    GCGCGGTATTACTTGGTGTAGCAGGCGCTAGAATTAAATCTACACCGACGATAGAATAGG
121 ---------+---------+---------+---------+---------+---------+   180

    CTAAACCTAATGTTTTTTTACCAAATAATTTGACGAAATGAAGTGCGATACGTCTACCAA
181 ---------+---------+---------+---------+---------+---------+   240

    GACCTGTTTTCACAAATCCTCTTGAAATGAAAAAGGCCATAGCAATTAACCATATACTAT
241 ---------+---------+---------+---------+---------+---------+   300

    TATTACCAAAACCAGCGACAGCCGTTTTCATGTCAACAATGCCAACGAGCACCATGATTG
301 ---------+---------+---------+---------+---------+---------+   360

    TAAATCCAATTACAGAGACAGCCCCAATTGGCATCGGTTGTGTAATACAAGCAATGATTG
361 ---------+---------+---------+---------+---------+---------+   420

    TCGCGACGAATATTGCGAACATATACCATGCTGTTGGATCCACAGCTTCCGGTTTAATAG
421 ---------+---------+---------+---------+---------+---------+   480

    GTGTAAGTGCCCAAATAAGGAGACCTACAACGATAGGGAGTATAAACTTACGATATTTAA
481 ---------+---------+---------+---------+---------+---------+   540

    CCGTGTTTTCCATGTTAAAACGTCCTTCTTTCTATGTTTTATACATATTTCAATTTAAGA
541 ---------+---------+---------+---------+---------+---------+   600
```

FIG. 2A

```
601   ATAAAGCTAACTACAAAAGATGTACAGTAATAATTAAATATAAAATTCAATTAACGAAAT   660
      ---------+---------+---------+---------+---------+---------+

661   CATTAATATAATTATTTTTCGAGAAGCGGTGAAGAACTGGTATAGTTGGTGTTTATTAAA   720
      ---------+---------+---------+---------+---------+---------+

721   TTTAAAAGATTTTGAAAATGAACTAATATACTAAGAAATTAATTGATACAAGTTAACTTC   780
      ---------+---------+---------+---------+---------+---------+

781   ATGCACTTGTATTCGTTATACTGTATATATTTTGCATAATAAAATAATAATATGAATTTT   840
      ---------+---------+---------+---------+---------+---------+

841   TGATAAATTTCATTGAATAAGAACTAAATTAGTTTATAATTTATTATTAGTATCCTGTGG   900
      ---------+---------+---------+---------+---------+---------+
                              RBS              S
901   ATATGACATAGAGTATAAGGAGGGGTTTTTATGAACAAAAATGTGTTGAAGTTTATGGTC   960
      ---------+---------+---------+---------+---------+---------+
                                    MetAsnLysAsnValLeuLysPheMetVal
                                                                    A
961   TTTATAATGTTATTAAATATCATCACACCTTTATTTAATAAAAATGAAGCATTTGCAGCA   1020
      ---------+---------+---------+---------+---------+---------+
      PheIleMetLeuLeuAsnIleIleThrProLeuPheAsnLysAsnGluAlaPheAla|Ala

1021  CGAGATATTTCATCAACGAATGTTACAGATTTAACTGTATCACCGTCTAAGATAGAAGAT   1080
      ---------+---------+---------+---------+---------+---------+
      ArgAspIleSerSerThrAsnValThrAspLeuThrValSerProSerLysIleGluAsp

1081  GGTGGTAAAACGACAGTAAAAATGACGTTCGACGATAAAAATGGAAAAATACAAAATGGT   1140
      ---------+---------+---------+---------+---------+---------+
      GlyGlyLysThrThrValLysMetThrPheAspAspLysAsnGlyLysIleGlnAsnGly

1141  GACATGATTAAAGTGGCATGGCCGACAAGCGGTACAGTAAAGATAGAGGGTTATAGTAAA   1200
      ---------+---------+---------+---------+---------+---------+
      AspMetIleLysValAlaTrpProThrSerGlyThrValLysIleGluGlyTyrSerLys
```

FIG. 2B

```
     ACAGTACCATTAACTGTTAAAGGTGAACAGGTGGGTCAAGCAGTTATTACACCAGACGGT
1201 ---------+---------+---------+---------+---------+---------+ 1260
     ThrValProLeuThrValLysGlyGluGlnValGlyGlnAlaValIleThrProAspGly

     GCAACAATTACATTCAATGATAAAGTAGAAAAATTAAGTGATGTTTCGGGATTTGCAGAA
1261 ---------+---------+---------+---------+---------+---------+ 1320
     AlaThrIleThrPheAsnAspLysValGluLysLeuSerAspValSerGlyPheAlaGlu

     TTTGAAGTACAAGGAAGAAATTTAACGCAAACAAATACTTTAGATGACAAAGTAGCTACG
1321 ---------+---------+---------+---------+---------+---------+ 1380
     PheGluValGlnGlyArgAsnLeuThrGlnThrAsnThrLeuAspAspLysValAlaThr

     ATAACATCTGGGAATAAATCAACGAATGTTATCGGTTGGATAAAAGTGAAGCGGGAACCA
1381 ---------+---------+---------+---------+---------+---------+ 1440
     IleThrSerGlyAsnLysSerThrAsnValIleGlyTrpIleLysValLysArgGluPro

     GTAGTGTTTCTAATTAATAAAAGCGGGAAGATATGCTACCAAGAAGATACGACACATGTA
1441 ---------+---------+---------+---------+---------+---------+ 1500
     ValValPheLeuIleAsnLysSerGlyLysIleCysTyrGlnGluAspThrThrHisVal

     CGATGGTTTTTAAATATTAACAATGAAAAAAGTTATGTATCGAAAGATATTACTATAAAG
1501 ---------+---------+---------+---------+---------+---------+ 1560
     ArgTrpPheLeuAsnIleAsnAsnGluLysSerTyrValSerLysAspIleThrIleLys

     GATCAGATTCAAGGTGGACAGCAGTTAGATTTAAGCACATTAAACATTAATGTGACAGGT
1561 ---------+---------+---------+---------+---------+---------+ 1620
     AspGlnIleGlnGlyGlyGlnGlnLeuAspLeuSerThrLeuAsnIleAsnValThrGly

     ACACATAGCAATTATTATAGTGGACAAAGTGCAATTACTGATTTTGAAAAAGCCTTTCCA
1621 ---------+---------+---------+---------+---------+---------+ 1680
     ThrHisSerAsnTyrTyrSerGlyGlnSerAlaIleThrAspPheGluLysAlaPhePro
```

FIG. 2C

```
     GGTTCTAAAATAACTGTTGATAATACGAAGAACACAATTGATGTAACAATTCCACAAGGC
1681 ---------+---------+---------+---------+---------+---------+ 1740
     GlySerLysIleThrValAspAsnThrLysAsnThrIleAspValThrIleProGlnGly

     TATGGGTCATATAATAGTTTTTCAATTAACTACAAAACCAAAATTACGAATGAACAGCAA
1741 ---------+---------+---------+---------+---------+---------+ 1800
     TyrGlySerTyrAsnSerPheSerIleAsnTyrLysThrLysIleThrAsnGluGlnGln
                                   HindIII
     AAAGAGTTTGTTAATAATTCACAAGCTTGGTATCAAGAGCATGGTAAGGAAGAAGTGAAC
1801 ---------+---------+---------+---------+---------+---------+ 1860
     LysGluPheValAsnAsnSerGlnAlaTrpTyrGlnGluHisGlyLysGluGluValAsn

     GGGAAATCATTTAATCATACTGTGCACAATATTAATGCTAATGCCGGTATTGAAGGTACT
1861 ---------+---------+---------+---------+---------+---------+ 1920
     GlyLysSerPheAsnHisThrValHisAsnIleAsnAlaAsnAlaGlyIleGluGlyThr

     GTAAAAGGTGAATTAAAAGTTTTAAAACAGGATAAAGATACCAAGGCTCCTATAGCTAAT
1921 ---------+---------+---------+---------+---------+---------+ 1980
     ValLysGlyGluLeuLysValLeuLysGlnAspLysAspThrLysAlaProIleAlaAsn

     GTAAAATTTAAACTTTCTAAAAAAGATGGATCAGTTGTAAAGGACAATCAAAAAGAAATT
1981 ---------+---------+---------+---------+---------+---------+ 2040
     ValLysPheLysLeuSerLysLysAspGlySerValValLysAspAsnGlnLysGluIle

     GAGATTATAACAGATGCAAACGGTATTGCTAATATTAAAGCGTTGCCTAGTGGAGACTAT
2041 ---------+---------+---------+---------+---------+---------+ 2100
     GluIleIleThrAspAlaAsnGlyIleAlaAsnIleLysAlaLeuProSerGlyAspTyr

     ATTTTAAAAGAAATAGAGGCGCCACGACCGTATACATTTGATAAGGATAAAGAATATCCG
2101 ---------+---------+---------+---------+---------+---------+ 2160
     IleLeuLysGluIleGluAlaProArgProTyrThrPheAspLysAspLysGluTyrPro

     TTTACTATGAAAGATACAGATAATCAGGGATATTTTACGACTATTGAAAATGCAAAAGCG
2161 ---------+---------+---------+---------+---------+---------+ 2220
     PheThrMetLysAspThrAspAsnGlnGlyTyrPheThrThrIleGluAsnAlaLysAla
```

FIG. 2D

```
      ATAGAAAAAACAAAAGATGTTTCTGCTCAAAAGGTTTGGGAAGGCACTCAAAAAGTGAAA
2221  ---------+---------+---------+---------+---------+---------+  2280
      IleGluLysThrLysAspValSerAlaGlnLysValTrpGluGlyThrGlnLysValLys

      CCAACGATTTATTTcAAGTTGTACAAACAAGATGACAATCAAAATACAACACCAGTAGAC
2281  ---------+---------+---------+---------+---------+---------+  2340
      ProThrIleTyrPheLysLeuTyrLysGlnAspAspAsnGlnAsnThrThrProValAsp
                                                 ┌─►5' end of insert in cCOLR6A
      AAAGCAGAGATTAAAAAATTAGAAGATGGAACGACAAAAGTGACATGGTCTAATCTTCCG
2341  ---------+---------+---------+---------+---------+---------+  2400
      LysAlaGluIleLysLysLeuGluAspGlyThrThrLysValThrTrpSerAsnLeuPro

      GAAAATGACAAAAAATGGCAAGGCTATTAAATATTTAGTTAAAGAAGTAAATGCTCAAGGT
2401  ---------+---------+---------+---------+---------+---------+  2460
      GluAsnAspLysAsnGlyLysAlaIleLysTyrLeuValLysGluValAsnAlaGlnGly

      GAAGATACAACACCAGAAGGATATACTAAAAAAGAAAATGGTTTAGTGGTTACTAATACT
2461  ---------+---------+---------+---------+---------+---------+  2520
      GluAspThrThrProGluGlyTyrThrLysLysGluAsnGlyLeuValValThrAsnThr
                     ┌─►B1
      GAAAAACCAATCGAAACAACATCAATTAGTGGTGAAAAAGTATGGGACGACAAAGACAAT
2521  ---------+---------+---------+---------+---------+---------+  2580
      GluLysProIleGluThrThrSerIleSerGlyGluLysValTrpAspAspLysAspAsn

      CAAGATGGTAAGAGACCAGAAAAAGTCAGTGTGAATTTATTGGCTAACGGGGAGAAAGTA
2581  ---------+---------+---------+---------+---------+---------+  2640
      GlnAspGlyLysArgProGluLysValSerValAsnLeuLeuAlaAsnGlyGluLysVal

      AAAACGTTAGACGTGACATCTGAAACAAACTGGAAGTACGAATTTAAAGACTTACCGAAG
2641  ---------+---------+---------+---------+---------+---------+  2700
      LysThrLeuAspValThrSerGluThrAsnTrpLysTyrGluPheLysAspLeuProLys
```

FIG. 2E

```
      TATGATGAAGGAAAGAAAATAGAATATACAGTGACCGAAGATCACGTAAAAGACTACACA
2701  ---------+---------+---------+---------+---------+---------+  2760
      TyrAspGluGlyLysLysIleGluTyrThrValThrGluAspHisValLysAspTyrThr

      ACAGACATCAACGGTACGACAATAACGAACAAGTATACACCAGGAGAGACATCGGCAACA
2761  ---------+---------+---------+---------+---------+---------+  2820
      ThrAspIleAsnGlyThrThrIleThrAsnLysTyrThrProGlyGluThrSerAlaThr

      GTAACAAAAAATTGGGATGACAATAATAACCAAGACGGAAAACGACCAACTGAAATCAAA
2821  ---------+---------+---------+---------+---------+---------+  2880
      ValThrLysAsnTrpAspAspAsnAsnAsnGlnAspGlyLysArgProThrGluIleLys

      GTTGAGTTATATCAAGACGGAAAAGCAACAGGAAAAACGGCAACATTAAATGAATCTAAT
2881  ---------+---------+---------+---------+---------+---------+  2940
      ValGluLeuTyrGlnAspGlyLysAlaThrGlyLysThrAlaThrLeuAsnGluSerAsn

      AACTGGACCCATACGTGGACAGGATTAGATGAAAAAGCAAAAGGACAACAAGTAAAATAC
2941  ---------+---------+---------+---------+---------+---------+  3000
      AsnTrpThrHisThrTrpThrGlyLeuAspGluLysAlaLysGlyGlnGlnValLysTyr

      ACAGTCGAGGAATTAACAAAGGTCAAAGGTTATACAACACATGTGGATAACAATGATATG
3001  ---------+---------+---------+---------+---------+---------+  3060
      ThrValGluGluLeuThrLysValLysGlyTyrThrThrHisValAspAsnAsnAspMet
                                         B2
      GGTAACTTGATTGTGACGAATAAATATACGCCAGAAACAACATCAATTAGTGGTGAAAAA
3061  ---------+---------+---------+---------+---------+---------+  3120
      GlyAsnLeuIleValThrAsnLysTyrThrProGluThrThrSerIleSerGlyGluLys

      GTATGGGACGACAAAGACAATCAAGATGGTAAGAGACCAGAAAAAGTCAGTGTGAATTTA
3121  ---------+---------+---------+---------+---------+---------+  3180
      ValTrpAspAspLysAspAsnGlnAspGlyLysArgProGluLysValSerValAsnLeu
```

FIG. 2F

```
      TTGGCTGATGGAGAGAAAGTAAAAACGTTAGACGTGACATCTGAAACAAACTGGAAGTAC
3181  ---------+---------+---------+---------+---------+---------+  3240
      LeuAlaAspGlyGluLysValLysThrLeuAspValThrSerGluThrAsnTrpLysTyr

      GAATTTAAAGACTTACCGAAGTATGATGAAGGAAAGAAAATAGAATATACAGTGACCGAA
3241  ---------+---------+---------+---------+---------+---------+  3300
      GluPheLysAspLeuProLysTyrAspGluGlyLysLysIleGluTyrThrValThrGlu

      GATCACGTAAAAGACTACACAACAGACATCAACGGTACGACAATAACGAACAAGTATACA
3301  ---------+---------+---------+---------+---------+---------+  3360
      AspHisValLysAspTyrThrThrAspIleAsnGlyThrThrIleThrAsnLysTyrThr

      CCAGGAGAGACATCGGCAACAGTAACAAAAAATTGGGATGACAATAATAACCAAGACGGA
3361  ---------+---------+---------+---------+---------+---------+  3420
      ProGlyGluThrSerAlaThrValThrLysAsnTrpAspAspAsnAsnAsnGlnAspGly

      AAACGACCAACTGAAATCAAAGTTGAGTTATATCAAGACGGAAAAGCAACAGGAAAAACG
3421  ---------+---------+---------+---------+---------+---------+  3480
      LysArgProThrGluIleLysValGluLeuTyrGlnAspGlyLysAlaThrGlyLysThr

      GCAACATTAAATGAATCTAATAACTGGACCCATACGTGGACAGGATTAGATGAAAAAGCA
3481  ---------+---------+---------+---------+---------+---------+  3540
      AlaThrLeuAsnGluSerAsnAsnTrpThrHisThrTrpThrGlyLeuAspGluLysAla

      AAAGGACAACAAGTAAAATACACAGTCGAGGAATTAACAAAGGTCAAAGGTTATACAACA
3541  ---------+---------+---------+---------+---------+---------+  3600
      LysGlyGlnGlnValLysTyrThrValGluGluLeuThrLysValLysGlyTyrThrThr
                                                            ┌─► B3
      CATGTGGATAACAATGATATGGGCAACTTGATTGTGACGAATAAATATACGCCAGAAACA
3601  ---------+---------+---------+---------+---------+---------+  3660
      HisValAspAsnAsnAspMetGlyAsnLeuIleValThrAsnLysTyrThrProGluThr
```

FIG. 2G

```
     ACATCAATTAGCGGTGAAAAAGTATGGGACGACAAAGACAATCAAGATGGTAAGAGACCA
3661 ---------+---------+---------+---------+---------+---------+ 3720
     ThrSerIleSerGlyGluLysValTrpAspAspLysAspAsnGlnAspGlyLysArgPro

     GAAAAAGTCAGTGTAAATTTATTGGCTAACGGAGAGAAAGTAAAAACGTTAGACGTGACA
3721 ---------+---------+---------+---------+---------+---------+ 3780
     GluLysValSerValAsnLeuLeuAlaAsnGlyGluLysValLysThrLeuAspValThr

     TCTGAAACAAACTGGAAGTACGAATTTAAAGACTTACCGAAGTATGATGAAGGAAAGAAA
3781 ---------+---------+---------+---------+---------+---------+ 3840
     SerGluThrAsnTrpLysTyrGluPheLysAspLeuProLysTyrAspGluGlyLysLys

     ATAGAATATACAGTGACCGAAGATCACGTAAAAGACTACACAACAGACATCAACGGTACG
3841 ---------+---------+---------+---------+---------+---------+ 3900
     IleGluTyrThrValThrGluAspHisValLysAspTyrThrThrAspIleAsnGlyThr
       3' end of insert in p16 <--
     ACAATAACGAACAAGTATACACCAGGAGAGACATCGGCAACAGTAACAAAAAATTGGGAT
3901 ---------+---------+---------+---------+---------+---------+ 3960
     ThrIleThrAsnLysTyrThrProGlyGluThrSerAlaThrValThrLysAsnTrpAsp

     GACAATAATAACCAAGACGGAAAACGACCAACTGAAATCAAAGTTGAGTTATATCAAGAT
3961 ---------+---------+---------+---------+---------+---------+ 4020
     AspAsnAsnAsnGlnAspGlyLysArgProThrGluIleLysValGluLeuTyrGlnAsp

     GGAAAAGCAACAGGAAAAACGGCAATATTAAATGAATCTAATAACTGGACACATACGTGG
4021 ---------+---------+---------+---------+---------+---------+ 4080
     GlyLysAlaThrGlyLysThrAlaIleLeuAsnGluSerAsnAsnTrpThrHisThrTrp

     ACAGGATTAGATGAAAAAGCAAAAGGACAACAAGTAAAATACACAGTCGATGAATTAACA
4081 ---------+---------+---------+---------+---------+---------+ 4140
     ThrGlyLeuAspGluLysAlaLysGlyGlnGlnValLysTyrThrValAspGluLeuThr
```

FIG. 2H

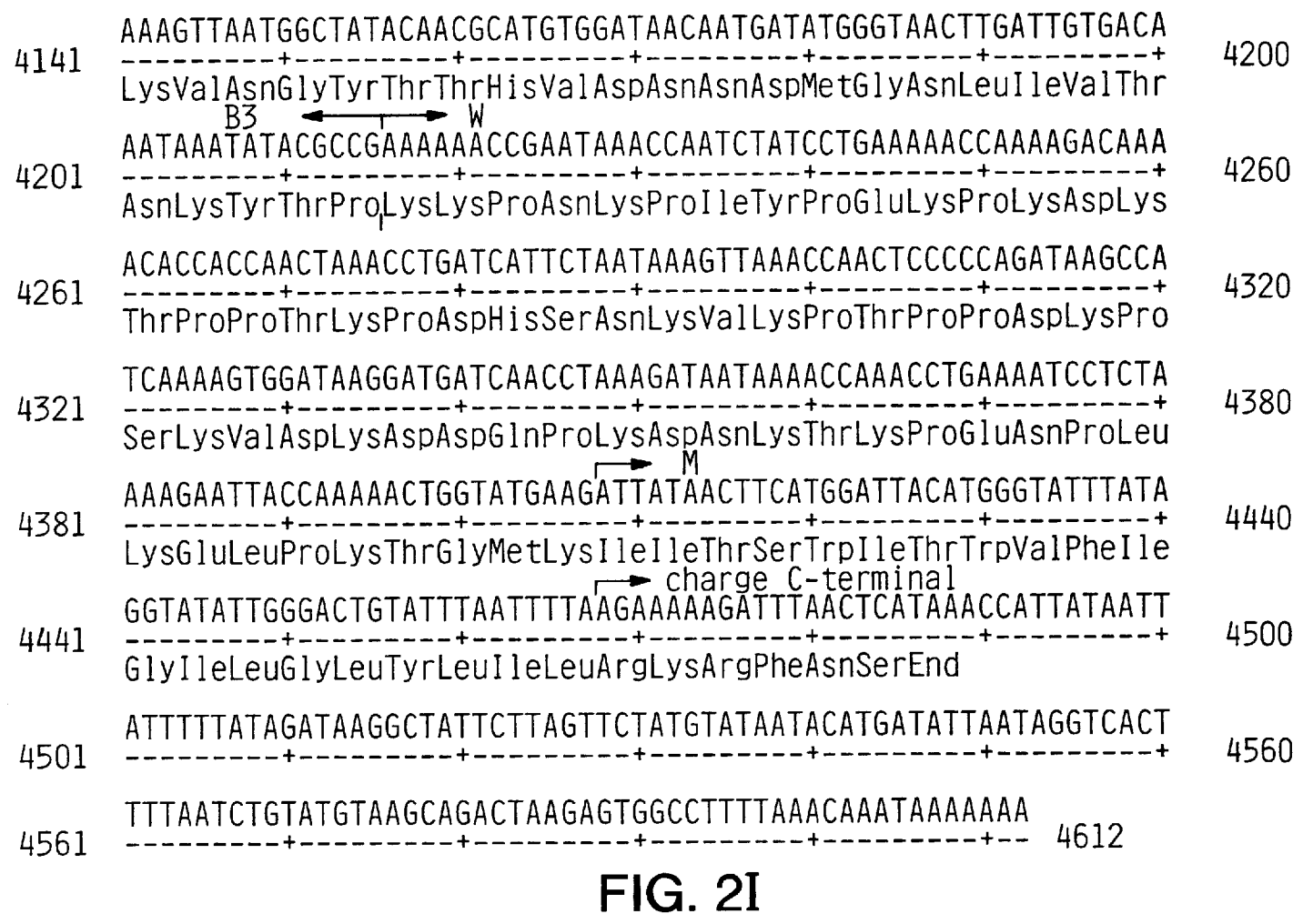

```
      AAAGTTAATGGCTATACAACGCATGTGGATAACAATGATATGGGTAACTTGATTGTGACA
4141  ---------+---------+---------+---------+---------+---------+  4200
      LysValAsnGlyTyrThrThrHisValAspAsnAsnAspMetGlyAsnLeuIleValThr
              B3                W
      AATAAATATACGCCGAAAAAACCGAATAAACCAATCTATCCTGAAAAACCAAAAGACAAA
4201  ---------+---------+---------+---------+---------+---------+  4260
      AsnLysTyrThrProLysLysProAsnLysProIleTyrProGluLysProLysAspLys

      ACACCACCAACTAAACCTGATCATTCTAATAAAGTTAAACCAACTCCCCCAGATAAGCCA
4261  ---------+---------+---------+---------+---------+---------+  4320
      ThrProProThrLysProAspHisSerAsnLysValLysProThrProProAspLysPro

      TCAAAAGTGGATAAGGATGATCAACCTAAAGATAATAAAACCAAACCTGAAAATCCTCTA
4321  ---------+---------+---------+---------+---------+---------+  4380
      SerLysValAspLysAspAspGlnProLysAspAsnLysThrLysProGluAsnProLeu
                                        M
      AAAGAATTACCAAAAACTGGTATGAAGATTATAACTTCATGGATTACATGGGTATTTATA
4381  ---------+---------+---------+---------+---------+---------+  4440
      LysGluLeuProLysThrGlyMetLysIleIleThrSerTrpIleThrTrpValPheIle
                                    charge C-terminal
      GGTATATTGGGACTGTATTTAATTTTAAGAAAAAGATTTAACTCATAAACCATTATAATT
4441  ---------+---------+---------+---------+---------+---------+  4500
      GlyIleLeuGlyLeuTyrLeuIleLeuArgLysArgPheAsnSerEnd

      ATTTTTATAGATAAGGCTATTCTTAGTTCTATGTATAATACATGATATTAATAGGTCACT
4501  ---------+---------+---------+---------+---------+---------+  4560

      TTTAATCTGTATGTAAGCAGACTAAGAGTGGCCTTTTAAACAAATAAAAAAA
4561  ---------+---------+---------+---------+---------+--  4612
```

FIG. 2I

COLLAGEN BINDING PROTEIN AS WELL AS ITS PREPARATION

This application is a continuation of application Ser. No. 07/861,804, filed Aug. 21, 1992, now abandoned.

DESCRIPTION

1. Technical Field

The present invention relates to a collagen binding protein as well as hybrid-DNA-molecules, e.g. plasmids or phages comprising a nucleotide sequence coding for said protein. Further the invention relates to microorganisms comprising said molecules and their use producing said protein, as well as the synthetic preparation of said protein. In particular the invention relates to a cloned gene encoding the *Staphylococcus aureus* collagen binding protein, or functionally active portions thereof, vectors containing the cloned gene or parts thereof, and microorganisms transformed by those vectors as well as the cloning of the gene which specify the biosynthesis of *Staphylococcus aureus* collagen binding protein (CBP) (also called the collagen receptor by Switalski et al 1989) and the use of organisms transformed with the cloned gene to produce CBP or CBP like proteins. The invention also describes the use of this gene for diagnostic purposes.

The object of the present invention is to obtain a collagen binding protein.

A further object is to obtain said protein by means of a genetic engineering technique by using e.g. a plasmid comprising a nucleotide sequence coding for said protein.

A further object is to obtain a possibility of preparing said protein by chemical synthesis.

Further objects will be apparent from the following description.

2. Background of the Invention

WO-Al-85/05553 discloses bacterial cell surface proteins having fibronectin, fibrinogen, collagen, and/or laminin binding ability. Thereby it is shown that different bacteria have an ability to bind to fibronectin, fibrinogen, collagen, and/or laminin.

Regarding the binding of collagen to *S. aureus* several studies have been reported (Carret et al 1985, Holderbaum et al 1985, Holderbaum et al 1986, Vercellotti et al 1985, Speziale et al 1986, Switalski et al 1989).

Switalski et al 1989 reported on the isolation and characterization of a *S. aureus* surface protein which they identified as a collagen receptor. Using lysostaphin to release the protein from the cell wall followed by ion exchange chromatography, ammonium sulfate precipitation and gel filtration it was possible to purify a protein with an apparent Mr of 135 kDa. It was also shown that antibodies raised against the 135 kDa protein inhibited the binding of collagen to *S. aureus* Cowan 1 cells.

DESCRIPTION OF THE INVENTION

It has now surprisingly been found possible to obtain a hybride-DNA-molecule comprising a nucleotide sequence coding for a protein or a polypeptide having collagen binding properties. As evident from below the following nucleotide sequence [SEQ ID NO: 1] is present in the gene coding for said protein.

ATGCACTTGT ATTCGTTATA CTGTATATAT TTTGCATAAT AAAATAATAA TATGAATTTT
TGATAAATTT CATTGAATAA GAACTAAATT AGTTTATAAT TTATTATTAG TATCCTGTGG
ATATGACATA GAGTATAAGG AGGGGTTTTT ATGAACAAAA ATGTGTTGAA GTTTATGGTC
TTTATAATGT TATTAAATAT CATCACACCT TTATTTAATA AAAATGAAGC ATTTGCAGCA
CGAGATATTT CATCAACGAA TGTTACAGAT TTAACTGTAT CACCGTCTAA GATAGAAGAT
GGTGGTAAAA CGACAGTAAA AATGACGTTC GACGATAAAA ATGGAAAAAT ACAAAATGGT
GACATGATTA AAGTGGCATG GCCGACAAGC GGTACAGTAA AGATAGAGGG TTATAGTAAA
ACAGTACCAT TAACTGTTAA AGGTGAACAG GTGGGTCAAG CAGTTATTAC ACCAGACGGT
GCAACAATTA CATTCAATGA TAAAGTAGAA AAATTAAGTG ATGTTTCGGG ATTTGCAGAA
TTTGAAGTAC AAGGAAGAAA TTTAACGCAA ACAAATACTT CAGATGACAA AGTAGCTACG
ATAACATCTG GGAATAAATC AACGAATGTT ACGGTTCATA AAAGTGAAGC GGGAACAAGT
AGTGTTTTCT ATTATAAAAC GGGAGATATG CTACCAGAAG ATACGACACA TGTACGATGG
TTTTTAAATA TTAACAATGA AAAAAGTTAT GTATCGAAAG ATATTACTAT AAAGGATCAG
ATTCAAGGTG GACAGCAGTT AGATTTAAGC ACATTAAACA TTAATGTGAC AGGTACACAT
AGCAATTATT ATAGTGGACA AAGTGCAATT ACTGATTTTG AAAAAGCCTT TCCAGGTTCT
AAAATAACTG TTGATAATAC GAAGAACACA ATTGATGTAA CAATTCCACA AGGCTATGGG
TCATATAATA GTTTTTCAAT TAACTACAAA ACCAAAATTA CGAATGAACA GCAAAAAGAG
TTTGTTAATA ATTCACAAGC TTGGTATCAA GAGCATGGTA AGGAAGAAGT GAACGGGAAA
TCATTTAATC ATACTGTGCA CAATATTAAT GCTAATGCCG GTATTGAAGG TACTGTAAAA
GGTGAATTAA AAGTTTTAAA ACAGGATAAA GATACCAAGG CTCCTATAGC TAATGTAAAA
TTTAAACTTT CTAAAAAAGA TGGATCAGTT GTAAAGGACA ATCAAAAAGA AATTGAGATT
ATAACAGATG CAAACGGTAT TGCTAATATT AAAGCGTTGC CTAGTGGAGA CTATATTTTA
AAAGAAATAG AGGCGCCACG ACCGTATACA TTTGATAAGG ATAAAGAATA TCCGTTTACT
ATGAAAGATA CAGATAATCA GGGATATTTT ACGACTATTG AAAATGCAAA AGCGATAGAA
AAAACAAAAG ATGTTTCTGC TCAAAAGGTT TGGGAAGGCA CTCAAAAAGT GAAACCAACG
ATTTATTTCA AGTTGTACAA ACAAGATGAC AATCAAAATA CAACACCAGT AGACAAAGCA
GAGATTAAAA AATTAGAAGA TGGAACGACA AAAGTGACAT GGTCTAATCT TCCGGAAAAT
GACAAAAATG GCAAGGCTAT TAAATATTTA GTTAAAGAAG TAAATGCTCA AGGTGAAGAT
ACAACACCAG AAGGATATAC TAAAAAAGAA AATGGTTTAG TGGTTACTAA TACTGAAAAA
CCAATCGAAA CAACATCAAT TAGTGGTGAA AAAGTATGGG ACGACAAAGA CAATCAAGAT
GGTAAGAGAC CAGAAAAAGT CAGTGTGAAT TTATTGGCTA ACGGGGAGAA AGTAAAAACG
TTAGACGTGA CATCTGAAAC AAACTGGAAG TACGAATTTA AAGACTTACC GAAGTATGAT
GAAGGAAAGA AAATAGAATA TACAGTGACC GAAGATCACG TAAAAGACTA CACAACAGAC
ATCAACGGTA CGACAATAAC GAACAAGTAT ACACCAGGAG AGACATCGGC AACAGTAACA
AAAAATTGGG ATGACAATAA TAACCAAGAC GGAAAACGAC CAACTGAAAT CAAAGTTGAG
TTATATCAAG ATGGAAAAGC AACAGGAAAA ACGGCAATAT TAAATGAATC TAATAACTGG

ACACATACGT GGACAGGATT AGATGAAAAA GCAAAAGGAC AACAAGTAAA ATACACAGTC GAGGAATTAA CAAAGGTCAA AGGTTATACA ACA-CATGTGG ATAACAATGA TATGGGTAAC TTGATTGTGA CGAATAAATA TACGCCAGAA ACAA-CATCAA TTAGTGGTGA AAAAGTATGG GACGACAAAG ACAATCAAGA TGGTAAGAGA CCA-GAAAAAG TCAGTGTGAA TTTATTGGCT GATGGAGAGA AAGTAAAAAC GTTAGACGTG ACATCTGAAA CAAACTGGAA GTACGAATTT AAAGACTTAC CGAAGTATGA TGAAGGAAAG AAAATAGAAT ATACAGTGAC CGAAGATCAC GTAAAAGACT ACACAACAGA CATCAACGGT ACGACAATAA CGAACAAGTA TACACCAGGA GAGACATCGG CAACAGTAAC AAAAAATTGG GAT-GACAATA ATAACCAAGA CGGAAAACGA CCAACTGAAA TCAAAGTTGA GTTATATCAA GATG-GAAAAG CAACAGGAAA AACGGCAATA TTAAATGAAT CTAATAACTG GACACATACG TGGA-CAGGAT TAGATGAAAA AGCAAAAGGA CAACAAGTAA AATACACAGT CGAGGAATTA ACAAAGGTCA AAGGTTATAC AACACATGTG GATAACAATG ATATGGGCAA CTTGATTGTG ACGAATAAAT ATACGCCAGA AACAACATCA ATTAGTGGTG AAAAAGTATG GGACGACAAA GACAATCAAG ATGGTAAGAG ACCAGAAAAA GTCAGTGTGA ATTTATTGGC TAACGGAGAG AAAG-TAAAAA CGTTAGACGT GACATCTGAA ACAAACTGGA AGTACGAATT TAAAGACTTA CCGAAGTATG ATGAAGGAAA GAAAATAGAA TATACAGTGA CCGAAGATCA CGTAAAAGAC TACA-CAACAG ACATCAACGG TACGACAATA ACGAACAAGT ATACACCAGG AGAGACATCG GCAACAGTAA CAAAAAATTG GGATGACAAT AATAACCAAG ACGGAAAACG ACCAACTGAA ATCAAAGTTG AGTTATATCA AGATGGAAAA GCAACAGGAA AAACGGCAAT ATTAAATGAA TCTAATAACT GGACACATAC GTGGACAGGA TTAGATGAAA AAGCAAAAGG ACAACAAGTA AAATACACAG TCGATGAATT AACAAAAGTT AATGGCTATA CAACGCATGT GGATAACAAT GATATGGGTA ACTTGATTGT GACAAATAAA TATACGCCGA AAAAACCGAA TAAACCAATC TATC-CTGAAA AACCAAAAGA CAAAACACCA CCAACTAAAC CTGATCATTC TAATAAAGTT AAAC-CAACTC CCCCAGATAA GCCATCAAAA GTGGATAAGG ATGATCAACC TAAAGATAAT AAAACCAAAC CTGAAAATCC TCTAAAAGAA TTACCAAAAA CTGGTATGAA GATTATAACT TCATG-GATTA CATGGGTATT TATAGGTATA TTGGGACTGT ATTTAATTTT AAGAAAAAGA TTTAACTCAT AAACCATTAT AATTATTTTT ATAGATAAGG CTATTCTTAG TTCTATGTAT AATA-CATGTA TATTAATAGG TCACTTTTAA TCTGTATGTA AGCAGACTAA GAGTGGCCTT TTAAACAAAT AAAAAAA whereby this nucleotide sequence encodes for the following protein starting at nucleotide no.151 in the reading above, whereby the prepresent nucleotides [SEQ ID NO: 2] shown in FIG. 2 are part of the signal system:

Ala

A r g A s p I l e S e r S e r T h r A s n - ValThrAspLeuThrValSerProSerLysIleGluAsp G l y G l y L y s T h r T h r V a l L y s M e t T h r - PheAspAspLysAsnGlyLysIleGlnAsnGly A s p M e t I l e L y s V a l A l a T r p P r o - ThrSerGlyThrValLysIleGluGlyTyrSerLys

T h r V a l P r o L e u T h r V a l L y s G l y - GluGlnValGlyGlnAlaValIleThrProAspGly A l a T h r I l e T h r P h e A s n A s p L y s V a l G - luLysLeuSerAspValSerGlyPheAlaGlu P h e G l u V a l G l n G l y A r g A s n L e u T h r - GlnThrAsnThrLeuAspAspLysvalAlaThr I l e T h r S e r G l y A s n L y s S e r T h r A s n - ValIleGlyTrpIleLysvalLysArgGluPro V a l V a l P h e L e u I l e A s n L y s S e r G - lyLysIleCysTyrGlnGluAspThrThrHisVal A r g T r p P h e L e u A s n I l e A s n A s n G l u - LysSerTyrValSerLysAspIleThrIleLys A s p G l n I l e G l n G l y G l y G l n G l n - LeuAspLeuSerThrLeuAsnIleAsnValThrGly T h r H i s S e r A s n T y r T y r S e r G - lyGlnSerAlaIleThrAspPheGluLysAlaPhePro G l y S e r L y s I l e T h r V a l - AspAsnThrLysAsnThrIleAspValThrIleProGlnGly T y r G l y S e r T y r A s n S e r P h e - SerIleAsnTyrLysThrLysIleThrAsnGluGlnGln L y s G l u P h e V a l A s n A s n S e r G l n A l a - TrpTyrGlnGluHisGlyLysGluGluValAsn G l y L y s S e r P h e A s n H i s T h r V a l - HisAsnIleAsnAlaAsnAlaGlyIleGluGlyThr V a l L y s G l y G l u L e u L y s V a l L e u L y s - GlnAspLysAspThrLysAlaProIleAlaAsn V a l L y s P h e L y s L e u - SerLysLysAspGlySerValValLysAspAsnGlnLysGluIle G l u I l e I l e T h r A s p A l a A s n G l y I l e A - laAsnIleLysAlaLeuProSerGlyAspTyr I l e L e u L y s G l u I l e G l u A l a P r o A r g - ProTyrThrPheAspLysAspLysGluTyrPro P h e T h r M e t L y s A s p T h r A s p A s n G l n G - lyTyrPheThrThrIleGluAsnAlaLysAla I l e G l u L y s T h r L y s A s p V a l S e r A l a - GlnLysValTrpGluGlyThrGlnLysValLys P r o T h r I l e T y r P h e L y s L e u T y r L y s - GlnAspAspAsnGlnAsnThrThrProValAsp L y s A l a G l u I l e L y s L y s L e u G l u A s p G - lyThrThrLysValThrTrpSerAsnLeuPro G l u A s n A s p L y s A s n G - lyLysAlaIleLysTyrLeuValLysGluValAsnAlaGlnGly G l u A s p T h r T h r P r o G l u G l y - TyrThrLysLysGluAsnGlyLeuValValThrAsnThr G l u L y s P r o I l e - G l u T h r T h r S e r I l e S e r G l y G l u L y s - ValTrpAspAspLysAspAsn G l n A s p G l y L y s A r g P r o G l u L y s - ValSerValAsnLeuLeuAlaAsnGlyGluLysval L y s T h r L e u A s p V a l T h r S e r - GluThrAsnTrpLysTyrGluPheLysAspLeuProLys T y r A s p G l u G l y L y s L y s I l e G l u - TyrThrValThrGluAspHisValLysAspTyrThr T h r A s p I l e A s n G l y T h r T h r I - leThrAsnLysTyrThrProGlyGluThrSerAlaThr V a l T h r L y s A s n T r p A s p A s p A s n A s - nAsnGlnAspGlyLysArgProThrGluIleLys V a l G l u L e u T y r G l n A s p G - lyLysAlaThrGlyLysThrAlaThrLeuAsnGluSerAsn A s n T r p T h r H i s T h r T r p T h r G - lyLeuAspGluLysAlaLysGlyGlnGlnValLysTyr T h r V a l G l u G l u L e u T h r L y s V a l L y s G - lyTyrThrThrHisValAspAsnAsnAspMet G l y A s n L e u I l e V a l T h r A s n L y - sTyrThrProGluThrThrSerIleSerGlyGluLys V a l T r p A s p A s p L y s A s p A s n G l n A s p G - lyLysArgProGluLysvalSerValAsnLeu LeuAlaAspGlyGluLysValLysThr-LeuAspValThrSerGluThrAsnTrpLysTyr
GluPheLysAspLeuProLysTyrAsp-GluGlyLysLysIleGluTyrThrValThrGlu
AspHisValLysAsp-TyrThrThrAspIleAsnGlyThrThrIleThrAsnLysTyrThr
ProGlyGluThrSerAlaThrValTh-rLysAsnTrpAspAspAsnAsnAsnGlnAspGly
LysArgProThrGluIleLysValG-luLeuTyrGlnAspGlyLysAlaThrGlyLysThr
AlaThrLeuAsnGluSerAsnAsn-TrpThrHisThrTrpThrGlyLeuAspGluLysAla
LysGlyGlnGlnValLysTyrThrVal-GluGluLeuThrLysValLysGlyTyrThrThr
HisValAspAsnAsnAspMetGlyAsn-LeuIleValThrAsnLysTyrThrProGluThr
ThrSerIleSerGlyGluLysValTr-pAspAspLysAspAsnGlnAspGlyLysArgPro
GluLysValSerValAsnLeuLeuA-laAsnGlyGluLysValLysThrLeuAspValThr
SerGluThrAsnTrpLysTyrG-luPheLysAspLeuProLysTyrAspGluGlyLysLys
IleGluTyrThrValThrGluAspHis-ValLysAspTyrThrThrAspIleAsnGlyThr
ThrIleThrAsnLysTyrThrProGly-GluThrSerAlaThrValThrLysAsnTrpAsp
AspAsnAsnAsnGlnAspGlyLysArg-ProThrGluIleLysValGluLeuTyrGlnAsp
GlyLysAlaThrG-lyLysThrAlaIleLeuAsnGluSerAsnAsnTrpThrHisThrTrp
ThrGlyLeuAspGluLysAlaLysG-lyGlnGlnValLysTyrThrValAspGluLeuThr
LysValAsnGlyTyrThrThrHisV-alAspAsnAsnAspMetGlyAsnLeuIleValThr
AsnLysTyrThr-ProLysLysProAsnLysProIleTyrProGluLysProLysAspLys
ThrProProThrLysProAspHisSer-AsnLysValLysProThrProProAspLysPro
SerLysValAspLysAspAspGln-ProLysAspAsnLysThrLysProGluAsnProLeu
LysGluLeuProLysThrGlyMetL-ysIleIleThrSerTrpIleThrTrpValPheIle
GlyIleLeuGlyLeuTyrLeuIleLeuArgLysArgPheAsnSer In the single letter amino acid sequence above the following abbreviations have been used A Ala, Alanine
R Arg, Arginine
N Asn, Asparagine
D Asp, Aspartic acid
C Cys, Cysteine
C Cys, Cystine
G Gly, Glycine
E Glu, Glutamic acid
Q Gln, Glutamine
H His, Histidine
I Ile, Isoleucine
L Leu, Leucine
K Lys, Lysine
M Met, Methionine
F Phe, Phenylalanine
P Pro, Proline
S Ser, Serine
T Thr, Threonine
W Trp, Tryptophan
Y Tyr, Tyrosine
V Val, Valine The invention further comprises a plasmid or phage comprising a nucleotide sequence coding for said collagen binding protein.

The invention further comprises a microorganism containing at least one hybrid-DNA-molecule according to the above. The plasmid pSAC104 in an *E. coli* strain TG1 has been deposited at the Deutsche Sammlung von Mikroorganismen (DSM), and has thereby been allocated the deposition number SM 6199. The present invention provides a cloned gene encoding the CBP having improved CBP-properties as compared with native CBP which is released and purified from *S. aureus* cells. The gene is derived from a *S. aureus* strain and inserted into a cloning vector. Cells of a procaryotic organism which have been transformed with recombinant vectors are disclosed.

The invention further provides the identification of the nucleotide sequence of the gene encoding the CBP here called the cbp-gene. The deduced amino acid sequence reveals a molecule with several distinct features resembling staphylococcal cell surface proteins.

The invention also provides a procedure for production and purification of the recombinant CBP. This is done in a way so that the molecule retains its collagen binding properties, thus this recombinant CBP resemblance the native unreleased *S. aureus* CBP.

The invention further provides the use of the cbp-gene for diagnostic purposes. Gene probes chosen to specifically recognize the presence of the cbp gene in clinical *S. aureus* isolates have been used. As an example, the correlation between the presence of CBP on the surface of *S. aureus* strains isolated from patient with septic arthritis could be verified by the presence of the cbp-gene in all tested strains.

Appropriate carrier proteins can be coupled to the amino acid sequence as well, such as IgG binding regions of protein A.

The invention will be described in the following with reference to the examples given, however, without being restricted thereto.

BRIEF DESCRIPTION OF THE FIGURES

FIGS. 2A–2I [SEQ ID NO: 8]: Nucleotide sequence and the deduced amino acid sequence of the assembled sequence from the insert in p 16 and cCOLR6A. The different regions are marked by arrows and sequences resembling ribosomal binding sites (RBS). The 5'end and 3'end of the insert in p 16 as well as the 5'end of the insert in cCOLR6A is indicated.

EXAMPLE 1

Figures 1A, 1B:
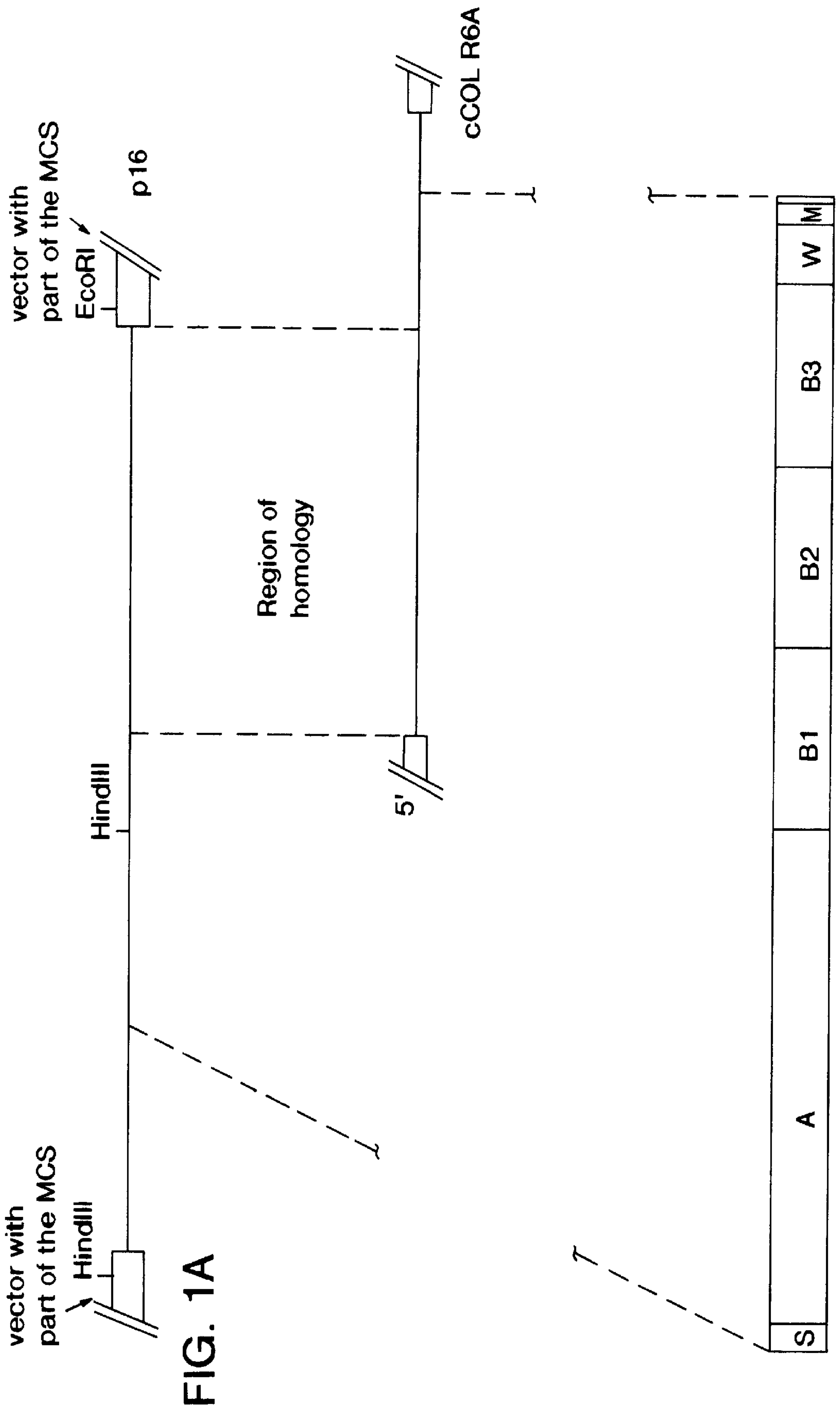
FIG. 1: (A), Simplified restriction map of the insert in p 16 and cCOLR6A showing the region of homology, MCS is an abbreviation for multi cloning site. (B), Schematic drawing of the cbp-gene encoding the different regions. S is the proposed signal sequence followed by region A and the repetitive B regions, W is the cell wall spanning region and M the membrane anchoring region.

Cloning and Identification of the cbp-gene in *E.coli*

In order to isolate the gene encoding *S. aureus* CBP two commercial available (Clontech laboratories, Inc. Palo Alto, Calif., USA) *S. aureus* strains (strain FDA 574 and FDA 485) were tested if they bound radioactively labelled collagen. This was done according to Switalski et al 1989. Strain 574 was found to bind collagen and therefore a gene library (obtained from the same company, cat. #XL 15016) of the same strain was screened for the expression of CBP activity. Using the suppliers protocol (in addition to this protocol the general work involving molecular genetic appropriate protocols found in "Current Protocols in Molecular Biology" Vol. 1 and 2, (edited by Ausubel, F. M., R. Brent, R. E. Kingston, D. D. Moore, I. G. Seidman, J. A. Smith, U. Struhl, Greene, Wiley Interscience), and "Molecular Cloning". A laboratory manual, (Maniatis, T., Fritsch, E. F. and J. Sambrook (1982) Cold Spring Harbor Laboratory Press, New York) were used) the recombinant lambda gt 11 phages were plated on *E. coli* strain Y1090. Agarplates with 10.000–100.000 PFU per 90 mm plate was chosen. The plaques from each plate were transferred by replicaplating to nitrocellulose (NC) filters (Schleicher & Schull). To detect plaques expressing CBP activity two different methods were used. In the first method the filters were preincubated in a solution containing 150 mM NaCl; 10 mM Tris pH 7,5; 1,36% milk powder (defatted) for 1 h at 37 degree C. (or overnight at room temperature (RT)). After the incubation the filters were transferred to the same type of solution as above but supplemented with 125-I labelled bovine type II collagen and the filters were incubated over night at RT. The following day the filters were washed 3x10 min in a solution containing 150 mM NaCl; 0,05% Tween 20 at 37 degree C., dried at RT and autoradiographed for several days to detect clones expressing collagen binding activity.

In an alternative screening method purified Fab-fragments from polyclonal rabbit IgG recognizing the native collagen receptor was used to detect clones expressing CBP-activity. This type Fab-fragment preparation had earlier been used by Switalski et al 1989 to identify and characterize the collagen receptor. In this alternative method the replica plated NC-filters were preincubated in a solution containing 150 mM NaCl; 10 mM Tris pH 7,5; 3% (W/V) bovine serum albumine (BSA) for 45 min at 37 degree to block unspecific binding. After blocking, the filters were transferred to a solution containing phosphate-buffered saline supplemented with Tween 20 to final conc. 0,05% (PBS-T) which also contained the rabbit anti-collagen receptor Fab-fragments in a dilution of 1:400. After 2,5 h incubation at RT the filters were washed 3x10 min in PBS-T followed by the addition of secondary goat anti-rabbit IgG alkaline phosphatase conjugate (Bio-Rad Laboratories, Richmond, Calif., USA, Cat. #170-6518) diluted 1:3000 in PBS-T to detect bound primary Fab-Fragments. After incubation for 1 h at RT the filters were washed 3x10 min in PBS-T. The bound labelled secondary antibodies were detected by a color reaction according to the manufacturer's instructions (Bio-Rad, Instructions for preparing the BCIP/NBT color development solution for use in the immun-blot alkaline phosphatase assay kit).

By the use the above described methods several recombinant lambda phages expressing CBP-activity could be identified and isolated.

Two of these were chosen for further studies. They were called lambda col 1 and lambda cCOLR6A respectively.

Subcloning lambda col 1: Purified lambda col 1 DNA was cleaved with EcoRI and the sticky ends were filled in using Klenow fragments together with the dNTP's. The blunt ended DNA-fragments originating from the *S. aureus* chromosome were ligated into Sma 1 cleaved pUC 18 (Pharmacia-LKB Biotechnology, Uppsala, Sweden). After transformation into freeze competent *E. coli* TG1 cells recombinant clones were tested for expression of the CBP. It was found that all clones expressing CBP harboured a recombinant plasmid with an insert of approx. 4 kb. One such clone called p 16 was chosen for further studies and a schematic map of the insert in this clone is shown in FIG. 1A.

In a similar way as lambda col 1 two other lambda clones were generated from the screening of the genomic library. Large scale cultures of pure positives were obtained and the DNA was isolated. EcoRI digestion of the clones resulted in inserts with two different sizes. Clone 1A had an insert of 3.2 kb and 3B had an insert of 4.5 kb. The larger of the two was used for further characterization. Purified insert DNA (1.5 kb) from λGT11 clone 3B was ligated to EcoRI digested puc18 and transformed into *E. coli* TB-1 cell creating subclone cCOLR6A. It was also subcloned into M13mp18/JM101 for sequencing.

$CsCl_2$ purified plasmid DNA from subclone cCOLR6A was then mapped using a variety restriction endonucleases. Pst1 digestion yielded two fragments 2.9 kb and 1.7 kb. Both fragments were sequenced. The 2.9 kb EcoRI-Pst1 fragment partially overlaps subclone λCOLL1. Subclone cCOLR6A contains all three repeats, the cell wall domain as well as the membrane spanning domain. A schematic map of the insert in this clone is shown in FIG. 1A.

Comparative restriction enzyme digestions together with hybridization experiments showed that p 16 and cCOLR6A partially overlapped each other (FIG. 1A).

EXAMPLE 2

DNA and Amino Acid Sequence Data

In order to determine the nucleotide sequence of the cbp-gene the protocol included in the Sequenase kit from (United States Biochemical Corporation, USA) was followed in order to analyze the insert in p 16 and cCOOL R6A. By comparing the nucleotide sequence from the inserts it was confirmed that the two inserts were partially homologous (FIG. 1A and FIG. 2). By assembling these sequences together and searching for open reading frames it was concluded that an open reading frame of 3.555 nt was used corresponding to a deduced amino acid sequence of 1185 amino acids (FIG. 2).

Within the deduced amino acid sequence there are several repetitive and homologous regions. This is schematically shown in FIG. 1B. Starting from the N-terminal end a structure resembling a signal sequence is revealed. This is in agreement with what one should expect since the CBP is a cell surface protein in *S. aureus*. Following this region, a region called A is found followed by a repetitive stretch of 187 amino acids called B 1, B 2 and B 3. Directly following these regions there is a region called W which consists of a repetitive, hydrophilic structure containing several proline residues. This region resembles a similar structure found in staphylococcal protein A (Guss et al 1984) and FnBPA (Sign äs et al 1989) as well as streptococcal protein G (Guss et al 1986) and M protein (Hollingshead et al 1986). This region is thought to mediate the binding of the protein to the cell wall. The amino acid sequence nearest to the C-terminal end consists of a long stretch of hydrophobic residues followed by some charged amino acids. This region called M is similar in structure to the C-terminal end of protein A, FnBP A, Protein G and M protein.

The predicted mol.wt of the deduced CBP is approx. 133 kd (including the postulated signal sequence, S) which is very close to the mol.wt of 135 kd reported for the native released receptor (Switalski et al 1989).

In order to construct a plasmid coding for the complete cbp-gene *S. aureus* FDA 574 chromosomal DNA was purified and double cleaved with Hind III/Pst 1. With the guidance of Southern Transfer experiments using a 32-P labelled oligonucleotide probe [SEQ ID NO: 3] (5'-ATTAAAGCGTTGCCTAGTGG-3') it was known that cleavage with these enzymes should generate an approx. 3,2 kb fragment corresponding to the 3'end of the cbp-gene. After cleavage with these enzymes the chromosomal DNA was electophoretically separated in an agarose gel. A gel slice roughly corresponding to right size was cut out and the DNA fragments eluted and purified. The purified fragments were ligated into pUC 18 previously double cleaved with Hind III/Pst 1. After ligation followed transformation into *E. coli* TG1 and the resulting recombinant clones were screened for obtaining the right fragment using colony hybridization with the same probe. One positive clone hybridizing with the radioactive probe was chosen for further studies. This clone called *E. coli* pSAC 100 was cleaved with Hind III and a purified approx. 1,8 kb Hind III fragment from p 16 (encoding the 5'end of the cbp-gene, FIG. 1A) was ligated into pSAC 100. After transformation into *E. coli* TG1 recombinant clones having the approx. 1,8 kb fragment in the right orientation was identified and isolated. One such clone called *E. coli* pSAC 104 was chosen for further studies. The insert in this clone should represent the complete cbp-gene. The clone was also positive when tested for expression of the CBP (see Example 3). This clone is deposited in Deutsche Sammlung von Mikroorganismen, Deposit number 6199.

EXAMPLE 3

Expression of the CBP in *E. coli*

Using the 125-I collagen binding assay as described by Switalski et al 1989 *E. coli* clones containing the whole cbp-gene or parts thereof were tested if lysates from these clones (containing CBP activity) could inhibit 125-I collagen to bind to the *S. aureus* Cowan I cells. The respective *E. coli* clone was grown in Luria Broth supplemented with ampicillin final conc. 50 microgram/ml over night. The bacteria were spun down and the supernatant discarded (this since most of the CBP activity was found intracellular). The bacterial pellet was resuspended in 1/10 of the original volume in a solution containing 50 mM Tris pH 8; 50 mM EDTA and lysozyme 1 mg/ml followed by incubation at 37 degree C. until complete lysis. The lysed bacteria were centrifuged to remove cellular debris and the supernatant taken care of. The ability of this supernatant (typical volume used was 100–200 microliter) to inhibit 125-I collagen to bind to Cowan I cells was measured. As a control *E. coli* TG1 pUC 18 treated in the same way was used. The presence of CBP activity could be measured as significant (in some cases up to 66%) reduction in bound radioactive collagen to the Cowan 1 cells when measured in a gamma counter. Three clones measured in this way *E. coli* TG1 p 16, *E. coli* TG1 pSAC 104 and *E. coli* TG1 pCA 1 showed high inhibitory activity as compared with the control *E. coli* TG1 pUC 18 which showed no significant inhibitory activity. This result is in contrast with the findings reported by Switalski et al 1989 which found that purified or partly purified native collagen receptor could not inhibit the binding of collagen to *S. aureus* Cowan 1 cells. The conclusion of this is that recombinant CBP expressed has retained more of its original features than the released protein from the staphylococci.

Although it was possible to detect CBP activity in the recombinant *E. coli* lysate it was not possible to affinity purify the CBP using immobilized collagen or gelatine. Although in “Western transfer” experiments with lysates from the above mentioned recombinant clones, using the Fab-fragments described in Example 1, was it possible to detect bands corresponding to high mol.wt. fragments. These were in the same size as expected from calculations using the deduced amino acid sequence.

EXAMPLE 4

Expression and of a CBP Fusionprotein which Retains the Collagen Binding Properties after Purification Been unsuccessful to affinity purify the recombinant produced CBP, using immobilized collagen, another approach was used. This approach was to fuse the cbp-gene or parts of the gene to another gene encoding a so called affinity tail (Methods in enzymology, Part 185). The affinity tail to be tested was the part from the protein A gene encoding the IgG-binding domains (Uhle'n et al 1984). Therefore a vector encoding the above mentioned domains from protein A was used. This vector called pNSEQ1, which was a gift from Dr. M. Uhle'n contains in addition to the IgG-binding domains (E, D, A, B and C) two multi cloning sites (MCS) which flank the IgG-binding domains. This makes it possible to chose a restriction enzyme that has a recognizion site in both the MCS which upon cleavage results in a release of (provided the restriction site is not present in the IgG-binding domains) a DNA fragment encoding the IgG-binding domains which can be purified and inserted into other vectors. Since the nucleotide sequence of the cbp-gene had been determined it was known that p 16 encoded the N-terminal part of the cbp-gene and the decision was to make a C-terminal fusion. This was done in the following way, the p 16 was cleaved with EcoRI (FIG. 1A) and a purified EcoRI DNA-fragment from pNSEQ1 encoding the IgG-binding part of protein A ligated into the plasmid. After transformation recombinant clones having the right orientation of the inserted protein A fragment were identified and isolated. One of these clones called *E. coli* pCA 1 was chosen for further studies. It was found that cell lysate of this clone in addition to inhibit collagen binding as measured in Example 3 also showed protein A IgG-binding activity. The next step was to try to affinity purify the presumtive fusionprotein on IgG-Sepharose FF (Pharmacia LKB Biotechnology, Uppsala, Sweden). Using the same manufacturer's Protein A manual it was possible to affinity purify the fusion protein from cell lysate. Using SDS-PAGE to analyse the purified protein it was shown that several bands corresponding to different mol.wt appeared when the gel was stained with Coomassie Brilliant Blue. However, the major band had the corresponding mol.wt of a full length fusion-protein as calculated from the deduced amino acid sequence. When measured for CBP activity this purified protein preparation could inhibit the binding of radioactive collagen to the *S. aureus* Cowan 1 cells as efficient as the corresponding cell lysate. This is also an improvement as compared with the result presented by Switalski et al 1989. The conclusion is that practizing the presented invention it is now possible to both produce and purify a *S. aureus* CBP which retains its biological properties in a better way as compared to earlier reported methods.

EXAMPLE 5

The Use of the CBP-gene as a Diagnostic Tool

Two oligonucleotides (JP-1 [SEQ ID NO: 4], 5'-AGT-GGT-TAC-TAA-TAC-TG-3' and JP-2[SEQ ID NO: 5], 5'-CAG-GAT-AGA-TIG-GTT-TA-3') complementary to regions of the CBP that flanked the repeats B1, B2, and B3 were constructed (Oligo's Etc.). Genomic DNA from 6 different *Staphyloccus aureus* strains that were known to bind $^{125}$I-collagen (Table 1) were isolated as previously described by Lindberg. Polymerase chain reaction (PCR) was performed with a Cetus/Perkin-Elmer DNA Thermocyler. Reaction mixtures (100 $\mu$l) contained 1 mM of each primer, 200 mM of each dNTP, 1 mM Tris-HCl (pH 8.3), 5 mM KCl, 15 mM $MgCl_2$, 0.001% gelatin, 3 $\mu$g template DNA, and 2.5 U AmpliTaq DNA polymerase. The reaction mixtures were overlayed with 100 $\mu$l of mineral oil and amplified for 30 cycles consisting of a 2 minute denaturation at 94° C., a 2 minute annealing period at 55° C., and a 3 minute extension period at 72° C. After amplification, 15 $\mu$l of the PCR products were analyzed on a 1% agarose gel (SeaKem GTG, FMC Inc., Rockland, Me.).

PCR analysis of the genomic DNA from the different *S. aureus* isolates revealed two distinctly different sized products. FDA 574, Cowan, and #13 all had gene products of 1677 bp, whereas Phillips, #7, and #14391 had gene products of 1118 bp. *S. aureus* Newman, a known non-collagen binder had no detectable PCR product. There is a direct correlation between the repeat size and the estimated molecular weight of the purified native collagen receptor from the different *S. aureus* strains tested. Upon further sequence analysis, it appears that a PCR product of 1677 bp corresponds to 3 repeat units, each 560 bp long. A PCR product of 1118 bp therefore corresponds to 2 repeats, each 560 bp long. These data correlate highly with the estimated molecular weight of purified native collagen receptors of 135 kd and 115 kd respectively.

Additional PCR analysis was carried out using primers JP-3 [SEQ ID NO: 6] (5'-ATA-TGA-ATT-CGA-GTA-TAA-GGA-GGG-GTT-3') and JP-4 [SEQ ID NO: 7] (5'-ATT-CTG-CAG-AGA-ACT-AAG-AAT-AGC-CTT-3'). These primers flank the intact CBP-gene at the 5' and 3' ends respectively. Using similar PCR parameters, the intact gene could be successfully isolated from *S. aureus* genomic DNA. Once again two distinctly different size gene products were discovered. Interestingly, the *S. aureus* isolates which had 3 repeats had a CBP-gene corresponding to 3.5 kb. The *S. aureus* strains which had only two repeats, had a CBP-gene of 3.0 kb. This work provides direct evidence that the size of the CBP-gene from various *S. aureus* isolates is directly proportional to the number of repeating units.

Expression of intact CBP-gene. The 3.5 kb PCR product which encompasses the intact gene (primers JP-3, JP-4) was cloned into the prokaryotic expression vector pKK223-3, Pharmacia-LKB. This vector contains an IPTG inducible tac promoter which drives expression of the cloned gene. Upon induction, coomassie staining of a 5–15% SDS-PAGE gel reveals a 135 kd protein. This matches the expected molecular weight of the native collagen receptor 4. This protein will be confirmed soon by western blot and a functional biological assay.

Immunological Relationship of the Collagen Adhesin from Different Clinical Isolates.

Figure 3:
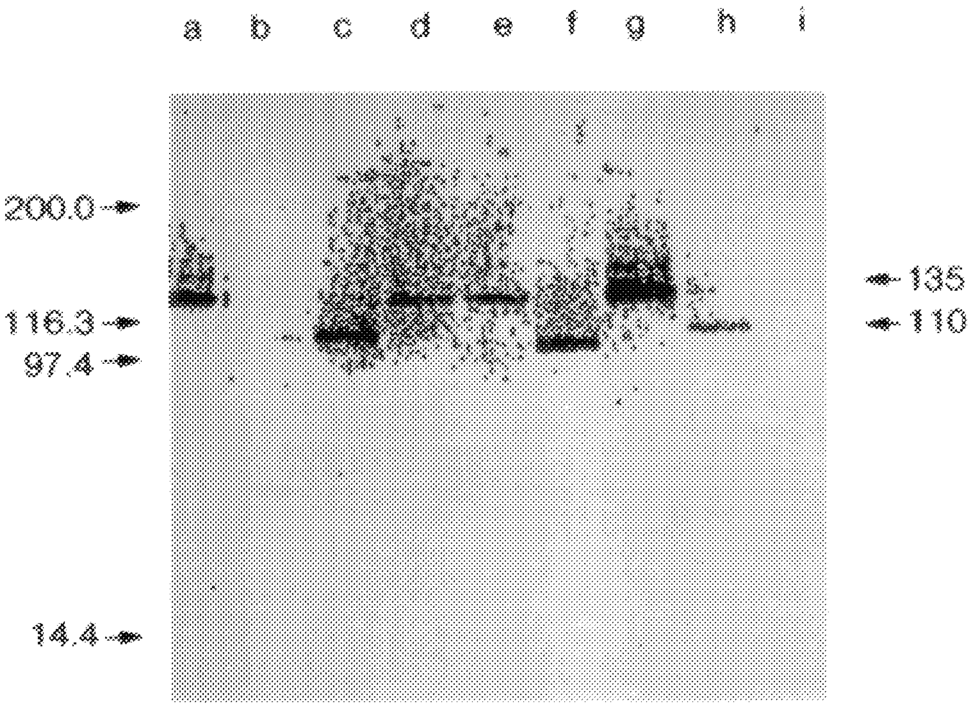
FIG. 3: Western blot of lysates of clinical isolates of *S. aureus* probed with anti-collagen adhesin antibodies. Lysostaphin lysates of strains were separated by gel electrophoresis, electroblotted onto an Immobilon-P membrane. Lanes a: Cowan, b: #7, c: #12, d: #13, e: #14, f: #15, g: #16, h: Phillips, and i: #9.

Previous results indicated that antibodies raised against whole cells of the collagen adhesin positive (CA+) strain *S. aureus* Cowan and its purified collagen adhesin effectively inhibited binding of $^{125}$I-labeled collagen to the homologous strain (Switalski et al., 1989). These antibodies also effectively inhibited binding of $^{125}$-I-collagen to all strains binding collagen, which indicates an immunological cross-reactivity of the collagen binding site. To examine the cell surface proteins recognized by these antibodies, they were used to probe Western blots of lysostaphin lysates prepared from different *S. aureus* isolates (FIG. 3). Lysostaphin digestion releases from the cell surface of *S. aureus* a number of proteins, around 30 bands can be visualized in the lysates by Coomassie Brilliant Blue staining of the gel (Switalski et al., 1989). The anti-adhesin antibodies recognized a component of $M_r$ 135 kd in the lysate of strain Cowan (FIG. 3, lane a), which is in agreement with our previous observations (Switalski et al., 1989). The major immunoreactive protein detected in the lysates of the other collagen adhesin positive strains (CA+) varied in molecular weight and was present as either 110 kd or 135 kd (FIG. 3, lanes b through h). No correlation was observed between the apparent size of the immunoreactive protein and the collagen binding capacity of a strain or its origin (bone, synovial fluid). None of the nine non-binding collagen *S. aureus* strains tested expressed an immunoreactive protein (FIG. 3, lane i).

Collagen Adhesin Mediated Attachment of Staphylococci to Collagenous Substrata.

Figure 4A:
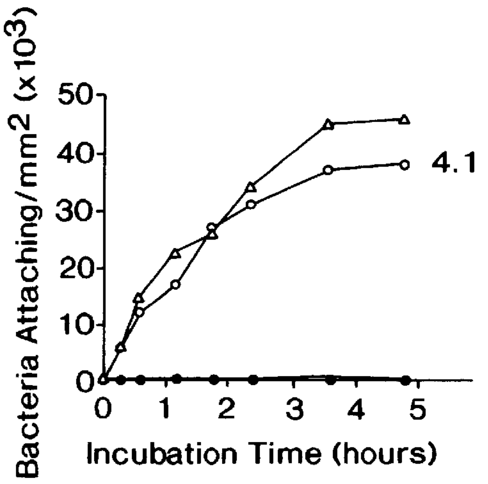
FIG. 4: Time dependent attachment of collagen adhesin positive and negative strains of *S. aureus* to collagen (panel A) and cartilage (panel C). Inhibition of this attachment by anti-adhesin antibodies (panels B and D, collagen and cartilage, respectively). $^{125}$I-labeled cells of two collagen adhesin positive strains—*S. aureus* Phillips (Δ) and #14 (O) and one adhesin negative strain—#9 (●) were incubated with collagen coated wells or with pieces of cartilage for indicated periods of time.
Figure 4B:
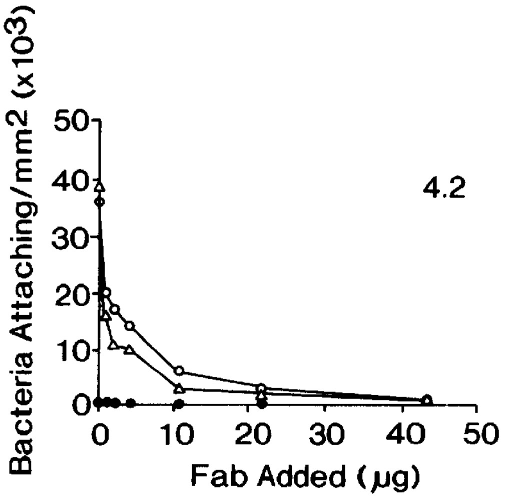

The relationship between the ability to express a collagen adhesin and the observed localization of an infection within collagen rich tissues prompted us to analyze the role of the cell surface adhesin in bacterial attachment to collagen containing substrates. We initially studied attachment of bacteria to surfaces coated with type II collagen. Results indicated that a collagen coated surface was an excellent attachment substrate for strains which express a surface localized collagen adhesin. The attachment is time dependent and saturable reaching an equilibrium after 3 hours of incubation (FIG. 4A). The number of attaching bacteria is not influenced by the size of the adhesin since strains #14 and Phillips, which either express a 135 kd or 110 kd adhesin respectively, attached in equal numbers to the collagen coated substrate. When bacteria were preincubated with anti-adhesin antibodies, against the collagen adhesin from *S. aureus* strain Cowan, attachment was inhibited in a concentration dependent manner (FIG. 4B). This confirmed previous observations on the immunological cross reactivity of the collagen binding site within the collagen adhesin. Attachment of the adhesin negative strains (CA−) was not affected by preincubation with the anti-adhesin antibodies.

Attachment of *S. aureus* to Cartilage.

Figure 4C:
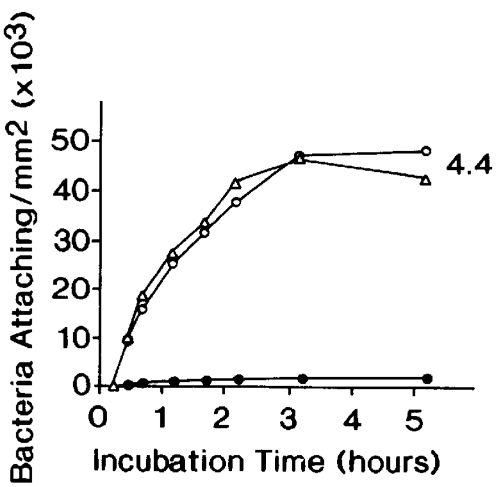
Figure 4D:
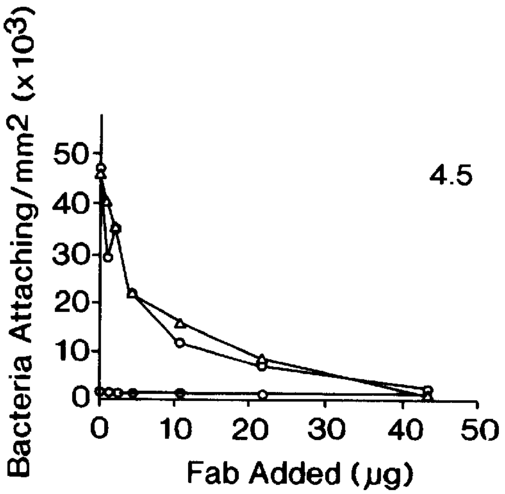

Subsequently, we studied the attachment of bacteria to cartilage, in a model mimicking the initial events in the development of infectious arthritis. In this model uniform pieces of cartilage were incubated with $^{125}$I-surfaced labeled *S. aureus*. Bovine nasal cartilage which is histologically identical to the bone cartilage was used in this study. Data obtained with cartilage tissue closely resembled those results of collagen coated surfaces. Only CA+ strains attached to cartilage (FIG. 4C), exhibiting kinetics analogous to those seen in CA+ strains attaching to collagen coated substrates. This attachment could be completely inhibited by preincubation with the anti-adhesin antibodies (FIG. 4D). These data indicate, that recognition of tissue collagen maybe sufficient for bacteria to colonize cartilage. Electron microscopy confirmed the quantitative observations presented previously. *S. aureus* strains which bind $^{125}$I-collagen and possess an immunoreactive protein on a Western blot, attached in large numbers to cartilage tissue, and can be seen preferentially attaching to collagen fibers. The number of attaching bacteria is drastically reduced in the presence of anti-adhesin antibodies. Electron microscopy observations indicated that attachment of bacteria to the bone tissue was indeed related to the ability to express a biologically functional collagen adhesin.

Creation of Artificial Bacteria

Figures 5A, 5B, 5C, 5D:
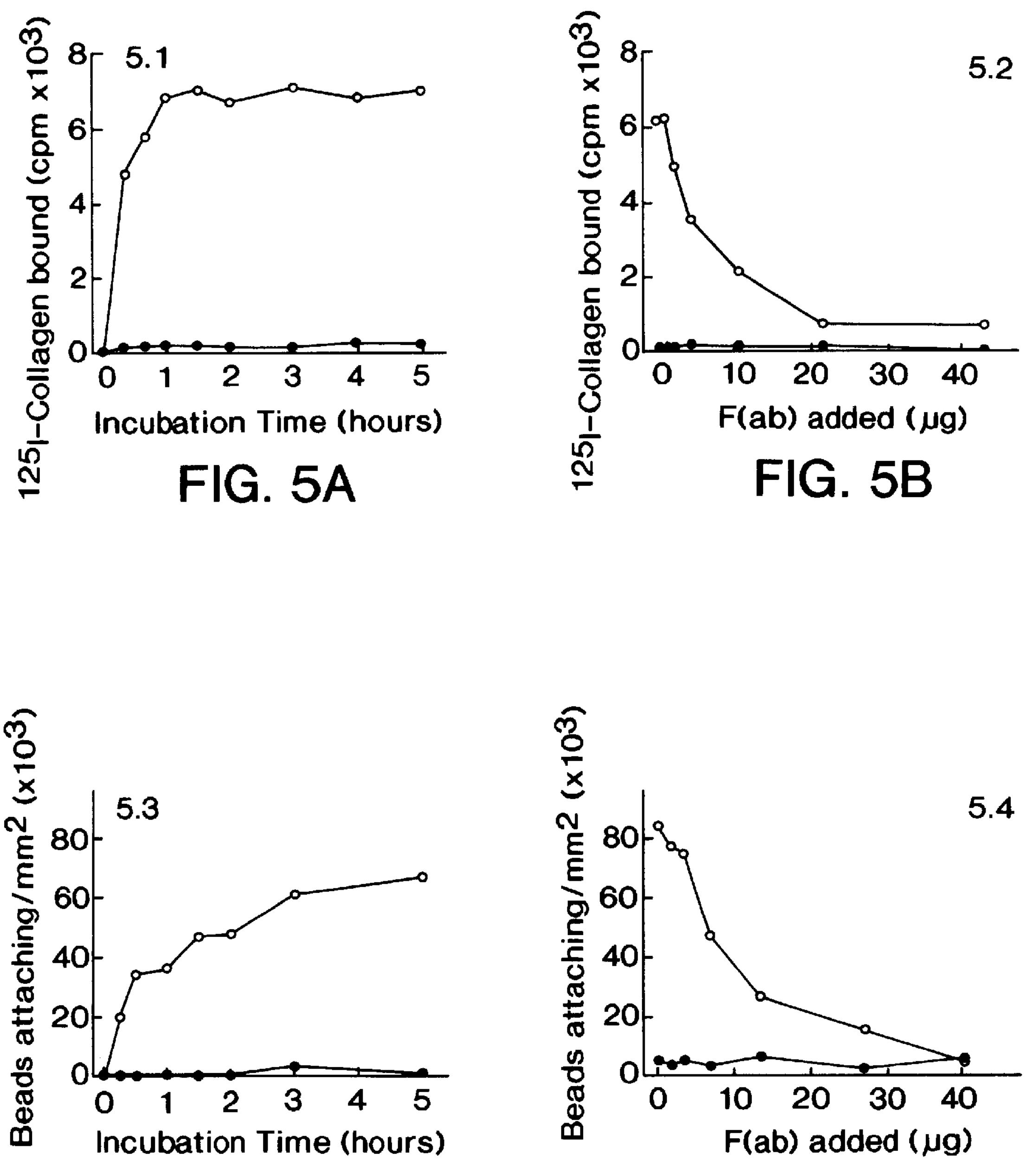
FIG. 5: Binding of $^{125}$I-labeled collagen or adhesion to cartilage by polystyrene beads coated either with the collagen adhesin (O) or a recombinant form of the *S. aureus* fibronectin receptor (●, ZZFR). Panel A—binding of $^{125}$I-collagen to protein coated beads as a function of time. Panel B—inhibition of binding of $^{125}$I-collagen by antibodies. Attachment of $^{125}$I-labeled beads to cartilage as a function of time (panel C) and inhibition of attachment of $^{125}$I-labeled beads to cartilage by antibodies (panel D). In this experiment 1 ug of adhesin protein was coupled to $10^8$ polystyrene beads. Control beads were coated with the same molar concentration of the fibronectin receptor. Unreacted sites on the beads were saturated with bovine serum albumin.

"Artificial bacteria" were prepared by covalently coating polystyrene beads (1.2 μm vs. staphylococci 0.8–1.0 μm in diameter) with the collagen adhesin protein. These beads were then tested in a series of experiments analogous to those performed with intact bacteria. The collagen adhesin (CA) coated beads, but not beads coated with a recombinant form of another staphylococcal cell surface component, the fibronectin receptor (Flock et al., 1987), bound $^{125}$I-collagen (FIG. 5A) in a manner similar to that of CA+ strains of *S. aureus* (Speziale et al., 1986). This binding was abolished by anti-CA antibodies, whereas preimmune antibodies did not effectively inhibit binding (FIG. 5B). When "artificial bacteria" were assayed for the ability to attach to collagen (data not shown) or cartilage, we found that CA beads adhered to the substrate in a time dependent manner, identical to that of CA+ strains of *S. aureus*, while beads coated with the fibronectin receptor did not adhere at significant levels (FIG. 5C). The anti-CA antibody inhibited the adhesion of CA beads to cartilage in a dose dependent fashion, whereas a preimmune antibodies had no effect (FIG. 5D). Once again the quantitative binding data was corroborated by electron microscopy observations. CA coated beads attached in large numbers to cartilage tissue, in particular to collagen fibers, while beads coated with the fibronectin receptor did not.

Localization of the Collagen Binding Domain within the Collagen Adhesin.

Figure 6:
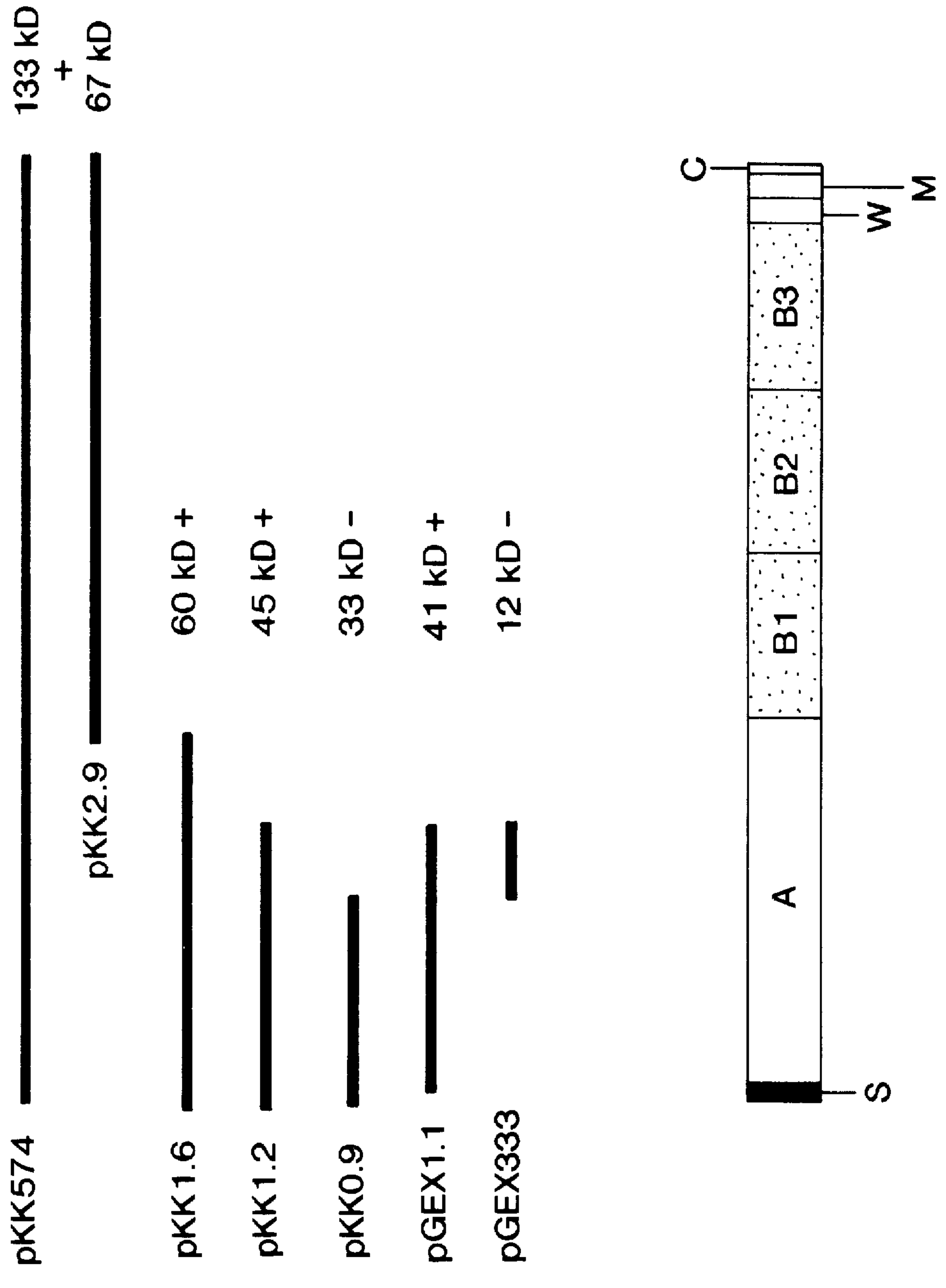
FIG. 6: Expression constructs utilized to localize the collagen binding domain within the *S. aureus* collagen adhesin.

Various expression constructs have been created in *E. coli* in effort to specifically localize the collagen binding domain. Two different types of expression vectors have been utilized in these experiments, pKK223-3 and pGEX-2T, the second of which results in the collagen adhesin fused to glutathione-S-transferase. To date the smallest region of the adhesin which has demonstratable collagen binding activity is contained within construct pGEX-1.1. This fusion protein is approximately 68 kDa, 41 kDa of which is represented by the collagen adhesin. As shown in FIG. 6, the collagen binding activity is located within the A domain of the cna gene.

The present collagen binding protein can be used for immunization, whereby the protein, preferably in combination with a fusion protein to create a large antigen to respond to, is injected in dosages causing immunological reaction in the host mammal. Thus the collagen binding protein can be used in vaccination of ruminants against mastitis caused by Staphylococcal infections.

Further, the collagen binding protein can be used to block an infection in an open skin wound by wound treatment using the collagen binding protein in a suspension. Thus the collagen binding protein can be used for the treatment of wounds, e.g. for blocking protein receptors, or for immunization (vaccination). In the latter case the host body produces specific antibodies, which can protect against invasion of bacterial strains comprising such a collagen binding protein. Hereby the antibodies block the adherence of the bacterial strains to damaged tissue. Treatment of septic arthritis is included as well.

Examples of colonizing of a tissue damage are:

a) colonizing of wounds in skin and connective tissue, which wounds have been caused by a mechanical trauma, chemical damage, and/or thermical damage;

b) colonizing of wounds on mucous membranes, such as in the mouth cavity, or in the mammary glands, urethra, or vagina;

c) colonizing on connective tissue proteins, which have been exposed by a minimal tissue damage (microlesion) in connection with epithelium and endothelium (mastitis, heart valve infection, hip exchange surgery).

When using the present CBP, or the polypeptide, for the purpose of immunization (vaccination) in mammals, including man, the protein, or polypeptide is dispersed in sterile, isotonic saline solution, optionally while adding a pharmaceutically acceptable dispersing agent. Different types of adjuvants can further be used in order to sustain the release in the tissue, and thus expose the protein or the peptide for a longer time to the immundefense system of a body.

A suitable dosage to obtain immunization is 0,5 to 5 μg of CBP, or polypeptide, per kg bodyweight and injection of immunization. In order to obtain a durable immunization, vaccination should be carried out at more than one consecutive occasion with an interval of 1 to 3 weeks, preferably at three occasions.

When using the present CBP, or polypeptide, for topical, local administration the protein is dispersed in an isotonic saline solution to a concentration of 25 to 250 μg per ml. The wounds are then treated with such an amount only to obtain a complete wetting of the wound surface. For an average wound thus only a couple of milliliters of solution are used in this way. After treatment using the protein solution the wounds are suitably washed with isotonic saline or another suitable wound treatment solution.

Further the collagen binding protein as well as the minimal collagen binding site polypeptide, of the present invention can be used to diagnose bacterial infections caused by Staphylococci strains, whereby a collagen binding protein of the present invention is immobilized on a solid carrier, such as small latex or Sepharose® beads, whereupon sera containing antibodies are allowed to pass and react with the CBP thus immobilized. The agglutination is then measured by known methods.

Further, the CBP, or the polypeptide can be used in an ELISA test (Enzyme Linked Immuno Sorbent Assay; E Engvall, Med. Biol. 55, 193, (1977). Hereby wells in a polystyrene microtitre plate are coated with the CBP, and incubated over night at 4° C. The plates are then thoroughly washed using PBS containing 0,05% TWEEN 20, and dried. Serial dilution of the patient serum were made in PBS-Tween, were added to the wells, and incubated at 30° C. for 1,5 hrs. After rinsing antihuman-IgG conjugated with an enzyme, or an antibovine-IgG conjugated with an enzyme, respectively, horseradishperoxidase or an alkaline phosphatasae, was added to the wells and incubated at 30° C. for 1,5 hrs, whereupon when the IgG has been bound thereto, and after rinsing, an enzyme substrate is added, a p-nitrophosphate in case of an alkaline phosphatase, or orthophenylene diamine substrate (OPD) in case a peroxidase has been used, respectively. The plates comprising the wells were thus then rinsed using a citrate buffer containing 0,055% OPD, and 0,005% $H_2O_2$, and incubated at 30° C. for 10 min. Enzyme reaction was stopped by adding a 4N solution of $H_2SO_4$ to each well. The colour development was measured using a spectrophotometer.

Depending on the type of enzyme substrate used a fluoroscense measurement can be used as well.

Another method to diagnose Staphylococcal infections is by using the DNA gene probe method based on the CBP nucleotide sequence or the polypeptide sequence. In the case of diagnozing a mastitis a milk sample is run through a membrane which collects bacteria present. Autolysis of the bacteria in alkali the released single stranded DNA binds to the membrane. The DNA gene probe, optionally labelled enzymatically, or by a radioactive isotope is then added to the membrane comprising the DNA sequence, whereby the DNA 10 gene probe attaches to the sequence where appearing. The enzyme or the radioactive isotope can then readily be determined by known methods.

Above the term collagen binding protein includes the polypeptide sequence as well, which polypeptide sequence forms the minimal collagen binding site of the complete protein.

References:

Carret, G., H. Emonard, G. Fardel, M. Druguet, D. Herbage, and J. P. Flandrois. 1985. Ann. Inst Pasteur (Paris) 136A:241–245.

Guss, B., M. Uhle'n, B. Nilsson, M. Lindberg, J. Sjöquist and J. Sjödahl. 1981. J. Biochem., 138, 413–420.

Guss, B., M. Eliasson, A. Olsson, M. Uhle'n, A.-K. Frej, H. Jörnvall, J.-I. Flock and M. Lindberg. 1986. EMBO J., 5, 1567–1575.

Holderbaum, D., R. A. Spech and L. A. Ehrhart. 1985. Collagen Relat. Res. 5:261–271.

Holderbaum, D., G. S. Hall and L. A. Ehrhart. 1986. Infect. Immun. 54:359–364.

Hollingshead, S. K., V. A. Fischetti and J. R. Scott. 1986. J. Biol. Chem. 261:1677–1686.

Signäs, S., G. Raucci, K. Jönsson, P.-E. Lindgren, G. M. Anantharamaiah, M. Höök and M. Lindberg. 1989. Proc. Nutl. Acad. Sci. USA. 86:699–703.

Speziale, P. G. Raucci, L. Visal, L. M. Switalski, R. Timpl and M. Höök. 1986. J. Bact. 167:77–81.

Switalski, L. M., P. Speziale and M. Höök. 1989. J. Biol. Chem. 264:21080–21086.

Uhle'n, M., B. Guss, B. Nilsson, S. Gatenbeck, L. Philipsson and M. Lindberg. 1984. J. Biol. Chem. 259:1695–1702.

Vercellotti, G. M., J. B. McCarthy, P. Lindholm, P. K. Peterson, H. S. Jacob and L. T. Furcht. 1985. Am. J. Pathol. 120:13–21.

We claim:

1. A plasmid pSAC104 as contained in the *E. coli* TG1 having the deposit number DSM 6199.

2. An *E. coli* strain expressing the protein encoded by the plasmid of claim 1.

3. A microorganism transformed by said plasmid of claim 1.

4. An isolated DNA-molecule characterized in that it comprises the following nucleotide sequence [SEQ ID NO: 1]:

ATGCACTTGT ATTCGTTATA CTGTATATAT TTTGCATAAT AAAATAATAA TATGAATTTT TGATAAATTT CATTGAATAA GAACTAAATT AGTTTATAAT TTATTATTAG TATCCTGTGG ATATGACATA GAGTATAAGG AGGGGTTTTT ATGAACAAAA ATGTGTTGAA GTTTATGGTC TTTATAATGT TATTAAATAT CATCACACCT TTATTTAATA AAAATGAAGC ATTTGCAGCA CGAGATATTT CATCAACGAA TGTTACAGAT TTAACTGTAT CACCGTCTAA GATAGAAGAT GGTGGTAAAA CGACAGTAAA AATGACGTTC GACGATAAAA ATGGAAAAAT ACAAAATGGT GACATGATTA AAGTGGCATG GCCGACAAGC GGTACAGTAA AGATAGAGGG TTATAGTAAA ACAGTACCAT TAACTGTTAA AGGTGAACAG GTGGGTCAAG CAGTTATTAC ACCAGACGGT GCAACAATTA CATTCAATGA TAAAGTAGAA AAATTAAGTG ATGTTTCGGG ATTTGCAGAA TTTGAAGTAC AAGGAAGAAA TTTAACGCAA ACAAATACTT CAGATGACAA AGTAGCTACG ATAACATCTG GGAATAAATC AACGAATGTT ACGGTTCATA AAAGTGAAGC GGGAACAAGT AGTGTTTTCT ATTATAAAAC GGGAGATATG CTACCAGAAG ATACGACACA TGTACGATGG TTTTTAAATA TTAACAATGA AAAAAGTTAT GTATCGAAAG ATATTACTAT AAAGGATCAG ATTCAAGGTG GACAGCAGTT AGATTTAAGC ACATTAAACA TTAATGTGAC AGGTACACAT AGCAATTATT ATAGTGGACA AAGTGCAATT ACTGATTTTG AAAAAGCCTT TCCAGGTTCT AAAATAACTG TTGATAATAC GAAGAACACA ATTGATGTAA CAATTCCACA AGGCTATGGG TCATATAATA GTTTTTCAAT TAACTACAAA ACCAAAATTA CGAATGAACA GCAAAAAGAG

TTTGTTAATA ATTCACAAGC TTGGTATCAA GAG-
CATGGTA AGGAAGAAGT GAACGGGAAA
TCATTTAATC ATACTGTGCA CAATATTAAT GCTAAT-
GCCG GTATTGAAGG TACTGTAAAA
GGTGAATTAA AAGTTTTAAA ACAGGATAAA
GATACCAAGG CTCCTATAGC TAATGTAAAA
TTTAAACTTT CTAAAAAAGA TGGATCAGTT
GTAAAGGACA ATCAAAAAGA AATTGAGATT
ATAACAGATG CAAACGGTAT TGCTAATATT
AAAGCGTTGC CTAGTGGAGA CTATATTTTA
AAAGAAATAG AGGCGCCACG ACCGTATACA
TTTGATAAGG ATAAAGAATA TCCGTTTACT
ATGAAAGATA CAGATAATCA GGGATATTTT ACGAC-
TATTG AAAATGCAAA AGCGATAGAA
AAAACAAAAG ATGTTTCTGC TCAAAAGGTT TGG-
GAAGGCA CTCAAAAAGT GAAACCAACG
ATTTATTTCA AGTTGTACAA ACAAGATGAC AAT-
CAAAATA CAACACCAGT AGACAAAGCA
GAGATTAAAA AATTAGAAGA TGGAACGACA
AAAGTGACAT GGTCTAATCT TCCGGAAAAT
GACAAAAATG GCAAGGCTAT TAAATATTTA
GTTAAAGAAG TAAATGCTCA AGGTGAAGAT
ACAACACCAG AAGGATATAC TAAAAAAGAA
AATGGTTTAG TGGTTACTAA TACTGAAAAA
CCAATCGAAA CAACATCAAT TAGTGGTGAA AAAG-
TATGGG ACGACAAAGA CAATCAAGAT
GGTAAGAGAC CAGAAAAAGT CAGTGTGAAT TTAT-
TGGCTA ACGGGGAGAA AGTAAAAACG
TTAGACGTGA CATCTGAAAC AAACTGGAAG TAC-
GAATTTA AAGACTTACC GAAGTATGAT
GAAGGAAAGA AAATAGAATA TACAGTGACC GAA-
GATCACG TAAAAGACTA CACAACAGAC
ATCAACGGTA CGACAATAAC GAACAAGTAT ACAC-
CAGGAG AGACATCGGC AACAGTAACA
AAAAATTGGG ATGACAATAA TAACCAAGAC
GGAAAACGAC CAACTGAAAT CAAAGTTGAG
TTATATCAAG ATGGAAAAGC AACAGGAAAA ACG-
GCAATAT TAAATGAATC TAATAACTGG
ACACATACGT GGACAGGATT AGATGAAAAA
GCAAAAGGAC AACAAGTAAA ATACACAGTC
GAGGAATTAA CAAAGGTCAA AGGTTATACA ACA-
CATGTGG ATAACAATGA TATGGGTAAC
TTGATTGTGA CGAATAAATA TACGCCAGAA ACAA-
CATCAA TTAGTGGTGA AAAAGTATGG
GACGACAAAG ACAATCAAGA TGGTAAGAGA CCA-
GAAAAAG TCAGTGTGAA TTTATTGGCT
GATGGAGAGA AAGTAAAAAC GTTAGACGTG
ACATCTGAAA CAAACTGGAA GTACGAATTT
AAAGACTTAC CGAAGTATGA TGAAGGAAAG
AAAATAGAAT ATACAGTGAC CGAAGATCAC
GTAAAAGACT ACACAACAGA CATCAACGGT
ACGACAATAA CGAACAAGTA TACACCAGGA
GAGACATCGG CAACAGTAAC AAAAAATTGG GAT-
GACAATA ATAACCAAGA CGGAAAACGA
CCAACTGAAA TCAAAGTTGA GTTATATCAA GATG-
GAAAAG CAACAGGAAA AACGGCAATA

TTAAATGAAT CTAATAACTG GACACATACG TGGA-
CAGGAT TAGATGAAAA AGCAAAAGGA
CAACAAGTAA AATACACAGT CGAGGAATTA
ACAAAGGTCA AAGGTTATAC AACACATGTG
GATAACAATG ATATGGGCAA CTTGATTGTG
ACGAATAAAT ATACGCCAGA AACAACATCA
ATTAGTGGTG AAAAAGTATG GGACGACAAA
GACAATCAAG ATGGTAAGAG ACCAGAAAAA
GTCAGTGTGA ATTTATTGGC TAACGGAGAG AAAG-
TAAAAA CGTTAGACGT GACATCTGAA
ACAAACTGGA AGTACGAATT TAAAGACTTA
CCGAAGTATG ATGAAGGAAA GAAAATAGAA
TATACAGTGA CCGAAGATCA CGTAAAAGAC TACA-
CAACAG ACATCAACGG TACGACAATA
ACGAACAAGT ATACACCAGG AGAGACATCG
GCAACAGTAA CAAAAAATTG GGATGACAAT
AATAACCAAG ACGGAAAACG ACCAACTGAA
ATCAAAGTTG AGTTATATCA AGATGGAAAA
GCAACAGGAA AAACGGCAAT ATTAAATGAA
TCTAATAACT GGACACATAC GTGGACAGGA
TTAGATGAAA AAGCAAAAGG ACAACAAGTA
AAATACACAG TCGATGAATT AACAAAAGTT
AATGGCTATA CAACGCATGT GGATAACAAT
GATATGGGTA ACTTGATTGT GACAAATAAA
TATACGCCGA AAAAACCGAA TAAACCAATC TATC-
CTGAAA AACCAAAAGA CAAAACACCA
CCAACTAAAC CTGATCATTC TAATAAAGTT AAAC-
CAACTC CCCCAGATAA GCCATCAAAA
GTGGATAAGG ATGATCAACC TAAAGATAAT
AAAACCAAAC CTGAAAATCC TCTAAAAGAA
TTACCAAAAA CTGGTATGAA GATTATAACT TCATG-
GATTA CATGGGTATT TATAGGTATA
TTGGGACTGT ATTTAATTTT AAGAAAAAGA
TTTAACTCAT AAACCATTAT AATTATTTTT
ATAGATAAGG CTATTCTTAG TTCTATGTAT AATA-
CATGTA TATTAATAGG TCACTTTTAA
TCTGTATGTA AGCAGACTAA GAGTGGCCTT
TTAAACAAAT AAAAAAA.

5. Plasmid or phage comprising one or more nucleotide sequences according to claim 4 [SEQ ID NO: 1].

6. Microorganism containing at least a plasmid or phage according to claim 5.

7. A method for producing a collagen binding protein or polypeptide, wherein a) at least one DNA-molecule according to claim 4 is introduced into a microorganism, b) said microorganism is cultivated in a growth promoting medium, and c) the protein thus formed is isolated by ion exchange chromatography, ammoniumsulphate precipitation and gel filtration.

8. A microorganism transformed by said hybrid-DNA-molecule of claim 4.

9. A microorganism transformed by said plasmid or phage of claim 5.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 3827 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
ATGCACTTGT ATTCGTTATA CTGTATATAT TTTGCATAAT AAAATAATAA TATGAATTTT    60
TGATAAATTT CATTGAATAA GAACTAAATT AGTTTATAAT TTATTATTAG TATCCTGTGG   120
ATATGACATA GAGTATAAGG AGGGGTTTTT ATGAACAAAA ATGTGTTGAA GTTTATGGTC   180
TTTATAATGT TATTAAATAT CATCACACCT TTATTTAATA AAAATGAAGC ATTTGCAGCA   240
CGAGATATTT CATCAACGAA TGTTACAGAT TTAACTGTAT CACCGTCTAA GATAGAAGAT   300
GGTGGTAAAA CGACAGTAAA AATGACGTTC GACGATAAAA ATGGAAAAAT ACAAAATGGT   360
GACATGATTA AAGTGGCATG GCCGACAAGC GGTACAGTAA AGATAGAGGG TTATAGTAAA   420
ACAGTACCAT TAACTGTTAA AGGTGAACAG GTGGGTCAAG CAGTTATTAC ACCAGACGGT   480
GCAACAATTA CATTCAATGA TAAAGTAGAA AAATTAAGTG ATGTTTCGGG ATTTGCAGAA   540
TTTGAAGTAC AAGGAAGAAA TTTAACGCAA ACAAATACTT CAGATGACAA AGTAGCTACG   600
ATAACATCTG GGAATAAATC AACGAATGTT ACGGTTCATA AAAGTGAAGC GGGAACAAGT   660
```

-continued

| | | | | | | |
|---|---|---|---|---|---|---|
| AGTGTTTTCT | ATTATAAAAC | GGGAGATATG | CTACCAGAAG | ATACGACACA | TGTACGATGG | 720 |
| TTTTTAAATA | TTAACAATGA | AAAAAGTTAT | GTATCGAAAG | ATATTACTAT | AAAGGATCAG | 780 |
| ATTCAAGGTG | GACAGCAGTT | AGATTTAAGC | ACATTAAACA | TTAATGTGAC | AGGTACACAT | 840 |
| AGCAATTATT | ATAGTGGACA | AAGTGCAATT | ACTGATTTTG | AAAAAGCCTT | TCCAGGTTCT | 900 |
| AAAATAACTG | TTGATAATAC | GAAGAACACA | ATTGATGTAA | CAATTCCACA | AGGCTATGGG | 960 |
| TCATATAATA | GTTTTTCAAT | TAACTACAAA | ACCAAAATTA | CGAATGAACA | GCAAAAAGAG | 1020 |
| TTTGTTAATA | ATTCACAAGC | TTGGTATCAA | GAGCATGGTA | AGGAAGAAGT | GAACGGGAAA | 1080 |
| TCATTTAATC | ATACTGTGCA | CAATATTAAT | GCTAATGCCG | GTATTGAAGG | TACTGTAAAA | 1140 |
| GGTGAATTAA | AAGTTTTAAA | ACAGGATAAA | GATACCAAGG | CTCCTATAGC | TAATGTAAAA | 1200 |
| TTTAAACTTT | CTAAAAAAGA | TGGATCAGTT | GTAAAGGACA | ATCAAAAAGA | AATTGAGATT | 1260 |
| ATAACAGATG | CAAACGGTAT | TGCTAATATT | AAAGCGTTGC | CTAGTGGAGA | CTATATTTTA | 1320 |
| AAAGAAATAG | AGGCGCCACG | ACCGTATACA | TTTGATAAGG | ATAAAGAATA | TCCGTTTACT | 1380 |
| ATGAAAGATA | CAGATAATCA | GGGATATTTT | ACGACTATTG | AAAATGCAAA | AGCGATAGAA | 1440 |
| AAAACAAAAG | ATGTTTCTGC | TCAAAAGGTT | TGGGAAGGCA | CTCAAAAAGT | GAAACCAACG | 1500 |
| ATTTATTTCA | AGTTGTACAA | ACAAGATGAC | AATCAAAATA | CAACACCAGT | AGACAAAGCA | 1560 |
| GAGATTAAAA | AATTAGAAGA | TGGAACGACA | AAAGTGACAT | GGTCTAATCT | TCCGGAAAAT | 1620 |
| GACAAAAATG | GCAAGGCTAT | TAAATATTTA | GTTAAAGAAG | TAAATGCTCA | AGGTGAAGAT | 1680 |
| ACAACACCAG | AAGGATATAC | TAAAAAAGAA | AATGGTTTAG | TGGTTACTAA | TACTGAAAAA | 1740 |
| CCAATCGAAA | CAACATCAAT | TAGTGGTGAA | AAAGTATGGG | ACGACAAAGA | CAATCAAGAT | 1800 |
| GGTAAGAGAC | CAGAAAAAGT | CAGTGTGAAT | TTATTGGCTA | ACGGGGAGAA | AGTAAAAACG | 1860 |
| TTAGACGTGA | CATCTGAAAC | AAACTGGAAG | TACGAATTTA | AAGACTTACC | GAAGTATGAT | 1920 |
| GAAGGAAAGA | AAATAGAATA | TACAGTGACC | GAAGATCACG | TAAAAGACTA | CACAACAGAC | 1980 |
| ATCAACGGTA | CGACAATAAC | GAACAAGTAT | ACACCAGGAG | AGACATCGGC | AACAGTAACA | 2040 |
| AAAAATTGGG | ATGACAATAA | TAACCAAGAC | GGAAAACGAC | CAACTGAAAT | CAAAGTTGAG | 2100 |
| TTATATCAAG | ATGGAAAAGC | AACAGGAAAA | ACGGCAATAT | TAAATGAATC | TAATAACTGG | 2160 |
| ACACATACGT | GGACAGGATT | AGATGAAAAA | GCAAAAGGAC | AACAAGTAAA | ATACACAGTC | 2220 |
| GAGGAATTAA | CAAAGGTCAA | AGGTTATACA | ACACATGTGG | ATAACAATGA | TATGGGTAAC | 2280 |
| TTGATTGTGA | CGAATAAATA | TACGCCAGAA | ACAACATCAA | TTAGTGGTGA | AAAAGTATGG | 2340 |
| GACGACAAAG | ACAATCAAGA | TGGTAAGAGA | CCAGAAAAAG | TCAGTGTGAA | TTTATTGGCT | 2400 |
| GATGGAGAGA | AAGTAAAAAC | GTTAGACGTG | ACATCTGAAA | CAAACTGGAA | GTACGAATTT | 2460 |
| AAAGACTTAC | CGAAGTATGA | TGAAGGAAAG | AAAATAGAAT | ATACAGTGAC | CGAAGATCAC | 2520 |
| GTAAAAGACT | ACACAACAGA | CATCAACGGT | ACGACAATAA | CGAACAAGTA | TACACCAGGA | 2580 |
| GAGACATCGG | CAACAGTAAC | AAAAAATTGG | GATGACAATA | ATAACCAAGA | CGGAAAACGA | 2640 |
| CCAACTGAAA | TCAAAGTTGA | GTTATATCAA | GATGGAAAAG | CAACAGGAAA | AACGGCAATA | 2700 |
| TTAAATGAAT | CTAATAACTG | GACACATACG | TGGACAGGAT | TAGATGAAAA | AGCAAAAGGA | 2760 |
| CAACAAGTAA | AATACACAGT | CGAGGAATTA | ACAAAGGTCA | AAGGTTATAC | AACACATGTG | 2820 |
| GATAACAATG | ATATGGGCAA | CTTGATTGTG | ACGAATAAAT | ATACGCCAGA | AACAACATCA | 2880 |
| ATTAGTGGTG | AAAAAGTATG | GGACGACAAA | GACAATCAAG | ATGGTAAGAG | ACCAGAAAAA | 2940 |
| GTCAGTGTGA | ATTTATTGGC | TAACGGAGAG | AAAGTAAAAA | CGTTAGACGT | GACATCTGAA | 3000 |
| ACAAACTGGA | AGTACGAATT | TAAAGACTTA | CCGAAGTATG | ATGAAGGAAA | GAAAATAGAA | 3060 |

-continued

```
TATACAGTGA CCGAAGATCA CGTAAAAGAC TACACAACAG ACATCAACGG TACGACAATA 3120
ACGAACAAGT ATACACCAGG AGAGACATCG GCAACAGTAA CAAAAAATTG GGATGACAAT 3180
AATAACCAAG ACGGAAAACG ACCAACTGAA ATCAAAGTTG AGTTATATCA AGATGGAAAA 3240
GCAACAGGAA AAACGGCAAT ATTAAATGAA TCTAATAACT GGACACATAC GTGGACAGGA 3300
TTAGATGAAA AAGCAAAAGG ACAACAAGTA AAATACACAG TCGATGAATT AACAAAAGTT 3360
AATGGCTATA CAACGCATGT GGATAACAAT GATATGGGTA ACTTGATTGT GACAAATAAA 3420
TATACGCCGA AAAAACCGAA TAAACCAATC TATCCTGAAA AACCAAAAGA CAAAACACCA 3480
CCAACTAAAC CTGATCATTC TAATAAAGTT AAACCAACTC CCCCAGATAA GCCATCAAAA 3540
GTGGATAAGG ATGATCAACC TAAAGATAAT AAAACCAAAC CTGAAAATCC TCTAAAAGAA 3600
TTACCAAAAA CTGGTATGAA GATTATAACT TCATGGATTA CATGGGTATT TATAGGTATA 3660
TTGGGACTGT ATTTAATTTT AAGAAAAAGA TTTAACTCAT AAACCATTAT AATTATTTTT 3720
ATAGATAAGG CTATTCTTAG TTCTATGTAT AATACATGTA TATTAATAGG TCACTTTTAA 3780
TCTGTATGTA AGCAGACTAA GAGTGGCCTT TTAAACAAAT AAAAAAA 3827
```

( 2 ) INFORMATION FOR SEQ ID NO:2:

( i ) SEQUENCE CHARACTERISTICS:
( A ) LENGTH: 1183 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Asn Lys Asn Val Leu Lys Phe Met Val Phe Ile Met Leu Leu Asn
 1               5                  10                  15

Ile Ile Thr Pro Leu Phe Asn Lys Asn Glu Ala Phe Ala Ala Arg Asp
            20                  25                  30

Ile Ser Ser Thr Asn Val Thr Asp Leu Thr Val Ser Pro Ser Lys Ile
        35                  40                  45

Glu Asp Gly Gly Lys Thr Thr Val Lys Met Thr Phe Asp Asp Lys Asn
    50                  55                  60

Gly Lys Ile Gln Asn Gly Asp Met Ile Lys Val Ala Trp Pro Thr Ser
65                  70                  75                  80

Gly Thr Val Lys Ile Glu Gly Tyr Ser Lys Thr Val Pro Leu Thr Val
                85                  90                  95

Lys Gly Glu Gln Val Gly Gln Ala Val Ile Thr Pro Asp Gly Ala Thr
            100                 105                 110

Ile Thr Phe Asn Asp Lys Val Glu Lys Leu Ser Asp Val Ser Gly Phe
        115                 120                 125

Ala Glu Phe Glu Val Gln Gly Arg Asn Leu Thr Gln Thr Asn Thr Ser
    130                 135                 140

Asp Asp Lys Val Ala Thr Ile Thr Ser Gly Asn Lys Ser Thr Asn Val
145                 150                 155                 160

Thr Val His Lys Ser Glu Ala Gly Thr Ser Ser Val Phe Tyr Tyr Lys
                165                 170                 175

Thr Gly Asp Met Leu Pro Glu Asp Thr Thr His Val Arg Trp Phe Leu
            180                 185                 190

Asn Ile Asn Asn Glu Lys Ser Tyr Val Ser Lys Asp Ile Thr Ile Lys
        195                 200                 205

Asp Gln Ile Gln Gly Gly Gln Gln Leu Asp Leu Ser Thr Leu Asn Ile
    210                 215                 220
```

-continued

| | | | | | | | | | | | | | | | |
|---|---|---|---|---|---|---|---|---|---|---|---|---|---|---|---|
| Asn | Val | Thr | Gly | Thr | His | Ser | Asn | Tyr | Tyr | Ser | Gly | Gln | Ser | Ala | Ile |
| 225 | | | | | 230 | | | | | 235 | | | | | 240 |
| Thr | Asp | Phe | Glu | Lys | Ala | Phe | Pro | Gly | Ser | Lys | Ile | Thr | Val | Asp | Asn |
| | | | | 245 | | | | | 250 | | | | | 255 | |
| Thr | Lys | Asn | Thr | Ile | Asp | Val | Thr | Ile | Pro | Gln | Gly | Tyr | Gly | Ser | Tyr |
| | | | 260 | | | | | 265 | | | | | 270 | | |
| Asn | Ser | Phe | Ser | Ile | Asn | Tyr | Lys | Thr | Lys | Ile | Thr | Asn | Glu | Gln | Gln |
| | | 275 | | | | | 280 | | | | | 285 | | | |
| Lys | Glu | Phe | Val | Asn | Asn | Ser | Gln | Ala | Trp | Tyr | Gln | Glu | His | Gly | Lys |
| | 290 | | | | | 295 | | | | | 300 | | | | |
| Glu | Glu | Val | Asn | Gly | Lys | Ser | Phe | Asn | His | Thr | Val | His | Asn | Ile | Asn |
| 305 | | | | | 310 | | | | | 315 | | | | | 320 |
| Ala | Asn | Ala | Gly | Ile | Glu | Gly | Thr | Val | Lys | Gly | Glu | Leu | Lys | Val | Leu |
| | | | | 325 | | | | | 330 | | | | | 335 | |
| Lys | Gln | Asp | Lys | Asp | Thr | Lys | Ala | Pro | Ile | Ala | Asn | Val | Lys | Phe | Lys |
| | | | 340 | | | | | 345 | | | | | 350 | | |
| Leu | Ser | Lys | Lys | Asp | Gly | Ser | Val | Val | Lys | Asp | Asn | Gln | Lys | Glu | Ile |
| | | 355 | | | | | 360 | | | | | 365 | | | |
| Glu | Ile | Ile | Thr | Asp | Ala | Asn | Gly | Ile | Ala | Asn | Ile | Lys | Ala | Leu | Pro |
| | 370 | | | | | 375 | | | | | 380 | | | | |
| Ser | Gly | Asp | Tyr | Ile | Leu | Lys | Glu | Ile | Glu | Ala | Pro | Arg | Pro | Tyr | Thr |
| 385 | | | | | 390 | | | | | 395 | | | | | 400 |
| Phe | Asp | Lys | Asp | Lys | Glu | Tyr | Pro | Phe | Thr | Met | Lys | Asp | Thr | Asp | Asn |
| | | | | 405 | | | | | 410 | | | | | 415 | |
| Gln | Gly | Tyr | Phe | Thr | Thr | Ile | Glu | Asn | Ala | Lys | Ala | Ile | Glu | Lys | Thr |
| | | | 420 | | | | | 425 | | | | | 430 | | |
| Lys | Asp | Val | Ser | Ala | Gln | Lys | Val | Trp | Glu | Gly | Thr | Gln | Lys | Val | Lys |
| | | 435 | | | | | 440 | | | | | 445 | | | |
| Pro | Thr | Ile | Tyr | Phe | Lys | Leu | Tyr | Lys | Gln | Asp | Asp | Asn | Gln | Asn | Thr |
| | 450 | | | | | 455 | | | | | 460 | | | | |
| Thr | Pro | Val | Asp | Lys | Ala | Glu | Ile | Lys | Lys | Leu | Glu | Asp | Gly | Thr | Thr |
| 465 | | | | | 470 | | | | | 475 | | | | | 480 |
| Lys | Val | Thr | Trp | Ser | Asn | Leu | Pro | Glu | Asn | Asp | Lys | Asn | Gly | Lys | Ala |
| | | | | 485 | | | | | 490 | | | | | 495 | |
| Ile | Lys | Tyr | Leu | Val | Lys | Glu | Val | Asn | Ala | Gln | Gly | Glu | Asp | Thr | Thr |
| | | | 500 | | | | | 505 | | | | | 510 | | |
| Pro | Glu | Gly | Tyr | Thr | Lys | Lys | Glu | Asn | Gly | Leu | Val | Val | Thr | Asn | Thr |
| | | 515 | | | | | 520 | | | | | 525 | | | |
| Glu | Lys | Pro | Ile | Glu | Thr | Thr | Ser | Ile | Ser | Gly | Glu | Lys | Val | Trp | Asp |
| | 530 | | | | | 535 | | | | | 540 | | | | |
| Asp | Lys | Asp | Asn | Gln | Asp | Gly | Lys | Arg | Pro | Glu | Lys | Val | Ser | Val | Asn |
| 545 | | | | | 550 | | | | | 555 | | | | | 560 |
| Leu | Leu | Ala | Asn | Gly | Glu | Lys | Val | Lys | Thr | Leu | Asp | Val | Thr | Ser | Glu |
| | | | | 565 | | | | | 570 | | | | | 575 | |
| Thr | Asn | Trp | Lys | Tyr | Glu | Phe | Lys | Asp | Leu | Pro | Lys | Tyr | Asp | Glu | Gly |
| | | | 580 | | | | | 585 | | | | | 590 | | |
| Lys | Lys | Ile | Glu | Tyr | Thr | Val | Thr | Glu | Asp | His | Val | Lys | Asp | Tyr | Thr |
| | | 595 | | | | | 600 | | | | | 605 | | | |
| Thr | Asp | Ile | Asn | Gly | Thr | Thr | Ile | Thr | Asn | Lys | Tyr | Thr | Pro | Gly | Glu |
| | 610 | | | | | 615 | | | | | 620 | | | | |
| Thr | Ser | Ala | Thr | Val | Thr | Lys | Asn | Trp | Asp | Asp | Asn | Asn | Asn | Gln | Asp |
| 625 | | | | | 630 | | | | | 635 | | | | | 640 |
| Gly | Lys | Arg | Pro | Thr | Glu | Ile | Lys | Val | Glu | Leu | Tyr | Gln | Asp | Gly | Lys |
| | | | | 645 | | | | | 650 | | | | | 655 | |

-continued

```
Ala Thr Gly Lys Thr Ala Ile Leu Asn Glu Ser Asn Asn Trp Thr His
            660                 665                 670

Thr Trp Thr Gly Leu Asp Glu Lys Ala Lys Gly Gln Gln Val Lys Tyr
        675                 680                 685

Thr Val Glu Glu Leu Thr Lys Val Lys Gly Tyr Thr Thr His Val Asp
    690                 695                 700

Asn Asn Asp Met Gly Asn Leu Ile Val Thr Asn Lys Tyr Thr Pro Glu
705                 710                 715                 720

Thr Thr Ser Ile Ser Gly Glu Lys Val Trp Asp Asp Lys Asp Asn Gln
                725                 730                 735

Asp Gly Lys Arg Pro Glu Lys Val Ser Val Asn Leu Leu Ala Asp Gly
            740                 745                 750

Glu Lys Val Lys Thr Leu Asp Val Thr Ser Glu Thr Asn Trp Lys Tyr
        755                 760                 765

Glu Phe Lys Asp Leu Pro Lys Tyr Asp Glu Gly Lys Lys Ile Glu Tyr
    770                 775                 780

Thr Val Thr Glu Asp His Val Lys Asp Tyr Thr Thr Asp Ile Asn Gly
785                 790                 795                 800

Thr Thr Ile Thr Asn Lys Tyr Thr Pro Gly Glu Thr Ser Ala Thr Val
                805                 810                 815

Thr Lys Asn Trp Asp Asp Asn Asn Asn Gln Asp Gly Lys Arg Pro Thr
            820                 825                 830

Glu Ile Lys Val Glu Leu Tyr Gln Asp Gly Lys Ala Thr Gly Lys Thr
        835                 840                 845

Ala Ile Leu Asn Glu Ser Asn Asn Trp Thr His Thr Trp Thr Gly Leu
    850                 855                 860

Asp Glu Lys Ala Lys Gly Gln Gln Val Lys Tyr Thr Val Glu Glu Leu
865                 870                 875                 880

Thr Lys Val Lys Gly Tyr Thr Thr His Val Asp Asn Asn Asp Met Gly
                885                 890                 895

Asn Leu Ile Val Thr Asn Lys Tyr Thr Pro Glu Thr Thr Ser Ile Ser
            900                 905                 910

Gly Glu Lys Val Trp Asp Asp Lys Asp Asn Gln Asp Gly Lys Arg Pro
        915                 920                 925

Glu Lys Val Ser Val Asn Leu Leu Ala Asn Gly Glu Lys Val Lys Thr
    930                 935                 940

Leu Asp Val Thr Ser Glu Thr Asn Trp Lys Tyr Glu Phe Lys Asp Leu
945                 950                 955                 960

Pro Lys Tyr Asp Glu Gly Lys Lys Ile Glu Tyr Thr Val Thr Glu Asp
                965                 970                 975

His Val Lys Asp Tyr Thr Thr Asp Ile Asn Gly Thr Thr Ile Thr Asn
            980                 985                 990

Lys Tyr Thr Pro Gly Glu Thr Ser Ala Thr Val Thr Lys Asn Trp Asp
        995                 1000                1005

Asp Asn Asn Asn Gln Asp Gly Lys Arg Pro Thr Glu Ile Lys Val Glu
    1010                1015                1020

Leu Tyr Gln Asp Gly Lys Ala Thr Gly Lys Thr Ala Ile Leu Asn Glu
1025                1030                1035                1040

Ser Asn Asn Trp Thr His Thr Trp Thr Gly Leu Asp Glu Lys Ala Lys
                1045                1050                1055

Gly Gln Gln Val Lys Tyr Thr Val Asp Glu Leu Thr Lys Val Asn Gly
            1060                1065                1070

Tyr Thr Thr His Val Asp Asn Asn Asp Met Gly Asn Leu Ile Val Thr
```

-continued 1075 1080 1085

Asn Lys Tyr Thr Pro Lys Lys Pro Asn Lys Pro Ile Tyr Pro Glu Lys
1090 1095 1100

Pro Lys Asp Lys Thr Pro Pro Thr Lys Pro Asp His Ser Asn Lys Val
1105 1110 1115 1120

Lys Pro Thr Pro Pro Asp Lys Pro Ser Lys Val Asp Lys Asp Asp Gln
1125 1130 1135

Pro Lys Asp Asn Lys Thr Lys Pro Glu Asn Pro Leu Lys Glu Leu Pro
1140 1145 1150

Lys Thr Gly Met Lys Ile Ile Thr Ser Trp Ile Thr Trp Val Phe Ile
1155 1160 1165

Gly Ile Leu Gly Leu Tyr Leu Ile Leu Arg Lys Arg Phe Asn Ser
1170 1175 1180

( 2 ) INFORMATION FOR SEQ ID NO:3:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

ATTAAAGCGT TGCCTAGTGG 20

( 2 ) INFORMATION FOR SEQ ID NO:4:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

AGTGGTTACT AATACTG 17

( 2 ) INFORMATION FOR SEQ ID NO:5:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 11
( D ) OTHER INFORMATION: /note= "Nucleotide 11 wherein N is I."

( x i ) SEQUENCE DESCRIPTION: SEQ ID NO:5:

CAGGATAGAT NGGTTTA 17

( 2 ) INFORMATION FOR SEQ ID NO:6:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear (ii) MOLECULE TYPE: DNA (genomic)

(xi) SEQUENCE DESCRIPTION: SEQ ID NO:6:

```
ATATGAATTC GAGTATAAGG AGGGGTT                                      27
```

(2) INFORMATION FOR SEQ ID NO:7:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

```
ATTCTGGACA GAACTAAGAA TAGCCTT                                      27
```

(2) INFORMATION FOR SEQ ID NO:8:

(i) SEQUENCE CHARACTERISTICS:
(A) LENGTH: 4612 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 931..4485

(xi) SEQUENCE DESCRIPTION: SEQ ID NO:8:

```
GGATCCCCAA TTCTTTTAAA ACTAGAAATT CACCCATTTT TCTTGATGAT TCGTCTTTTG    60

GTTTCGAACC AAATGATTCA GAAAGTGATT TGATAATTGG GAACATGATT CCACCAGCAC   120

GCGCGGTATT ACTTGGTGTA GCAGGCGCTA GAATTAAATC TACACCGACG ATAGAATAGG   180

CTAAACCTAA TGTTTTTTTA CCAAATAATT TGACGAAATG AAGTGCGATA CGTCTACCAA   240

GACCTGTTTT CACAAATCCT CTTGAAATGA AAAAGGCCAT AGCAATTAAC CATATACTAT   300

TATTACCAAA ACCAGCGACA GCCGTTTTCA TGTCAACAAT GCCAACGAGC ACCATGATTG   360

TAAATCCAAT TACAGAGACA GCCCCAATTG GCATCGGTTG TGTAATACAA GCAATGATTG   420

TCGCGACGAA TATTGCGAAC ATATACCATG CTGTTGGATC CACAGCTTCC GGTTTAATAG   480

GTGTAAGTGC CCAAATAAGG AGACCTACAA CGATAGGGAG TATAAACTTA CGATATTTAA   540

CCGTGTTTTC CATGTTAAAA CGTCCTTCTT TCTATGTTTT ATACATATTT CAATTTAAGA   600

ATAAAGCTAA CTACAAAAGA TGTACAGTAA TAATTAAATA TAAAATTCAA TTAACGAAAT   660

CATTAATATA ATTATTTTTC GAGAAGCGGT GAAGAACTGG TATAGTTGGT GTTTATTAAA   720

TTTAAAAGAT TTTGAAAATG AACTAATATA CTAAGAAATT AATTGATACA AGTTAACTTC   780

ATGCACTTGT ATTCGTTATA CTGTATATAT TTTGCATAAT AAAATAATAA TATGAATTTT   840

TGATAAATTT CATTGAATAA GAACTAAATT AGTTTATAAT TTATTATTAG TATCCTGTGG   900

ATATGACATA GAGTATAAGG AGGGGTTTTT ATG AAC AAA AAT GTG TTG AAG TTT    954
                                 Met Asn Lys Asn Val Leu Lys Phe
                                     1185                1190

ATG GTC TTT ATA ATG TTA TTA AAT ATC ATC ACA CCT TTA TTT AAT AAA   1002
Met Val Phe Ile Met Leu Leu Asn Ile Ile Thr Pro Leu Phe Asn Lys
            1195                1200                1205

AAT GAA GCA TTT GCA GCA CGA GAT ATT TCA TCA ACG AAT GTT ACA GAT   1050
Asn Glu Ala Phe Ala Ala Arg Asp Ile Ser Ser Thr Asn Val Thr Asp
        1210                1215                1220
```

-continued

```
TTA ACT GTA TCA CCG TCT AAG ATA GAA GAT GGT GGT AAA ACG ACA GTA     1098
Leu Thr Val Ser Pro Ser Lys Ile Glu Asp Gly Gly Lys Thr Thr Val
    1225                1230                1235

AAA ATG ACG TTC GAC GAT AAA AAT GGA AAA ATA CAA AAT GGT GAC ATG     1146
Lys Met Thr Phe Asp Asp Lys Asn Gly Lys Ile Gln Asn Gly Asp Met
1240                1245                1250                1255

ATT AAA GTG GCA TGG CCG ACA AGC GGT ACA GTA AAG ATA GAG GGT TAT     1194
Ile Lys Val Ala Trp Pro Thr Ser Gly Thr Val Lys Ile Glu Gly Tyr
                1260                1265                1270

AGT AAA ACA GTA CCA TTA ACT GTT AAA GGT GAA CAG GTG GGT CAA GCA     1242
Ser Lys Thr Val Pro Leu Thr Val Lys Gly Glu Gln Val Gly Gln Ala
            1275                1280                1285

GTT ATT ACA CCA GAC GGT GCA ACA ATT ACA TTC AAT GAT AAA GTA GAA     1290
Val Ile Thr Pro Asp Gly Ala Thr Ile Thr Phe Asn Asp Lys Val Glu
        1290                1295                1300

AAA TTA AGT GAT GTT TCG GGA TTT GCA GAA TTT GAA GTA CAA GGA AGA     1338
Lys Leu Ser Asp Val Ser Gly Phe Ala Glu Phe Glu Val Gln Gly Arg
    1305                1310                1315

AAT TTA ACG CAA ACA AAT ACT TTA GAT GAC AAA GTA GCT ACG ATA ACA     1386
Asn Leu Thr Gln Thr Asn Thr Leu Asp Asp Lys Val Ala Thr Ile Thr
1320                1325                1330                1335

TCT GGG AAT AAA TCA ACG AAT GTT ATC GGT TGG ATA AAA GTG AAG CGG     1434
Ser Gly Asn Lys Ser Thr Asn Val Ile Gly Trp Ile Lys Val Lys Arg
                1340                1345                1350

GAA CCA GTA GTG TTT CTA ATT AAT AAA AGC GGG AAG ATA TGC TAC CAA     1482
Glu Pro Val Val Phe Leu Ile Asn Lys Ser Gly Lys Ile Cys Tyr Gln
            1355                1360                1365

GAA GAT ACG ACA CAT GTA CGA TGG TTT TTA AAT ATT AAC AAT GAA AAA     1530
Glu Asp Thr Thr His Val Arg Trp Phe Leu Asn Ile Asn Asn Glu Lys
        1370                1375                1380

AGT TAT GTA TCG AAA GAT ATT ACT ATA AAG GAT CAG ATT CAA GGT GGA     1578
Ser Tyr Val Ser Lys Asp Ile Thr Ile Lys Asp Gln Ile Gln Gly Gly
    1385                1390                1395

CAG CAG TTA GAT TTA AGC ACA TTA AAC ATT AAT GTG ACA GGT ACA CAT     1626
Gln Gln Leu Asp Leu Ser Thr Leu Asn Ile Asn Val Thr Gly Thr His
1400                1405                1410                1415

AGC AAT TAT TAT AGT GGA CAA AGT GCA ATT ACT GAT TTT GAA AAA GCC     1674
Ser Asn Tyr Tyr Ser Gly Gln Ser Ala Ile Thr Asp Phe Glu Lys Ala
                1420                1425                1430

TTT CCA GGT TCT AAA ATA ACT GTT GAT AAT ACG AAG AAC ACA ATT GAT     1722
Phe Pro Gly Ser Lys Ile Thr Val Asp Asn Thr Lys Asn Thr Ile Asp
            1435                1440                1445

GTA ACA ATT CCA CAA GGC TAT GGG TCA TAT AAT AGT TTT TCA ATT AAC     1770
Val Thr Ile Pro Gln Gly Tyr Gly Ser Tyr Asn Ser Phe Ser Ile Asn
        1450                1455                1460

TAC AAA ACC AAA ATT ACG AAT GAA CAG CAA AAA GAG TTT GTT AAT AAT     1818
Tyr Lys Thr Lys Ile Thr Asn Glu Gln Gln Lys Glu Phe Val Asn Asn
    1465                1470                1475

TCA CAA GCT TGG TAT CAA GAG CAT GGT AAG GAA GAA GTG AAC GGG AAA     1866
Ser Gln Ala Trp Tyr Gln Glu His Gly Lys Glu Glu Val Asn Gly Lys
1480                1485                1490                1495

TCA TTT AAT CAT ACT GTG CAC AAT ATT AAT GCT AAT GCC GGT ATT GAA     1914
Ser Phe Asn His Thr Val His Asn Ile Asn Ala Asn Ala Gly Ile Glu
                1500                1505                1510

GGT ACT GTA AAA GGT GAA TTA AAA GTT TTA AAA CAG GAT AAA GAT ACC     1962
Gly Thr Val Lys Gly Glu Leu Lys Val Leu Lys Gln Asp Lys Asp Thr
            1515                1520                1525

AAG GCT CCT ATA GCT AAT GTA AAA TTT AAA CTT TCT AAA AAA GAT GGA     2010
Lys Ala Pro Ile Ala Asn Val Lys Phe Lys Leu Ser Lys Lys Asp Gly
        1530                1535                1540
```

-continued

TCA GTT GTA AAG GAC AAT CAA AAA GAA ATT GAG ATT ATA ACA GAT GCA 2058
Ser Val Val Lys Asp Asn Gln Lys Glu Ile Glu Ile Ile Thr Asp Ala
1545 1550 1555

AAC GGT ATT GCT AAT ATT AAA GCG TTG CCT AGT GGA GAC TAT ATT TTA 2106
Asn Gly Ile Ala Asn Ile Lys Ala Leu Pro Ser Gly Asp Tyr Ile Leu
1560 1565 1570 1575

AAA GAA ATA GAG GCG CCA CGA CCG TAT ACA TTT GAT AAG GAT AAA GAA 2154
Lys Glu Ile Glu Ala Pro Arg Pro Tyr Thr Phe Asp Lys Asp Lys Glu
1580 1585 1590

TAT CCG TTT ACT ATG AAA GAT ACA GAT AAT CAG GGA TAT TTT ACG ACT 2202
Tyr Pro Phe Thr Met Lys Asp Thr Asp Asn Gln Gly Tyr Phe Thr Thr
1595 1600 1605

ATT GAA AAT GCA AAA GCG ATA GAA AAA ACA AAA GAT GTT TCT GCT CAA 2250
Ile Glu Asn Ala Lys Ala Ile Glu Lys Thr Lys Asp Val Ser Ala Gln
1610 1615 1620

AAG GTT TGG GAA GGC ACT CAA AAA GTG AAA CCA ACG ATT TAT TTC AAG 2298
Lys Val Trp Glu Gly Thr Gln Lys Val Lys Pro Thr Ile Tyr Phe Lys
1625 1630 1635

TTG TAC AAA CAA GAT GAC AAT CAA AAT ACA ACA CCA GTA GAC AAA GCA 2346
Leu Tyr Lys Gln Asp Asp Asn Gln Asn Thr Thr Pro Val Asp Lys Ala
1640 1645 1650 1655

GAG ATT AAA AAA TTA GAA GAT GGA ACG ACA AAA GTG ACA TGG TCT AAT 2394
Glu Ile Lys Lys Leu Glu Asp Gly Thr Thr Lys Val Thr Trp Ser Asn
1660 1665 1670

CTT CCG GAA AAT GAC AAA AAT GGC AAG GCT ATT AAA TAT TTA GTT AAA 2442
Leu Pro Glu Asn Asp Lys Asn Gly Lys Ala Ile Lys Tyr Leu Val Lys
1675 1680 1685

GAA GTA AAT GCT CAA GGT GAA GAT ACA ACA CCA GAA GGA TAT ACT AAA 2490
Glu Val Asn Ala Gln Gly Glu Asp Thr Thr Pro Glu Gly Tyr Thr Lys
1690 1695 1700

AAA GAA AAT GGT TTA GTG GTT ACT AAT ACT GAA AAA CCA ATC GAA ACA 2538
Lys Glu Asn Gly Leu Val Val Thr Asn Thr Glu Lys Pro Ile Glu Thr
1705 1710 1715

ACA TCA ATT AGT GGT GAA AAA GTA TGG GAC GAC AAA GAC AAT CAA GAT 2586
Thr Ser Ile Ser Gly Glu Lys Val Trp Asp Asp Lys Asp Asn Gln Asp
1720 1725 1730 1735

GGT AAG AGA CCA GAA AAA GTC AGT GTG AAT TTA TTG GCT AAC GGG GAG 2634
Gly Lys Arg Pro Glu Lys Val Ser Val Asn Leu Leu Ala Asn Gly Glu
1740 1745 1750

AAA GTA AAA ACG TTA GAC GTG ACA TCT GAA ACA AAC TGG AAG TAC GAA 2682
Lys Val Lys Thr Leu Asp Val Thr Ser Glu Thr Asn Trp Lys Tyr Glu
1755 1760 1765

TTT AAA GAC TTA CCG AAG TAT GAT GAA GGA AAG AAA ATA GAA TAT ACA 2730
Phe Lys Asp Leu Pro Lys Tyr Asp Glu Gly Lys Lys Ile Glu Tyr Thr
1770 1775 1780

GTG ACC GAA GAT CAC GTA AAA GAC TAC ACA ACA GAC ATC AAC GGT ACG 2778
Val Thr Glu Asp His Val Lys Asp Tyr Thr Thr Asp Ile Asn Gly Thr
1785 1790 1795

ACA ATA ACG AAC AAG TAT ACA CCA GGA GAG ACA TCG GCA ACA GTA ACA 2826
Thr Ile Thr Asn Lys Tyr Thr Pro Gly Glu Thr Ser Ala Thr Val Thr
1800 1805 1810 1815

AAA AAT TGG GAT GAC AAT AAT AAC CAA GAC GGA AAA CGA CCA ACT GAA 2874
Lys Asn Trp Asp Asp Asn Asn Asn Gln Asp Gly Lys Arg Pro Thr Glu
1820 1825 1830

ATC AAA GTT GAG TTA TAT CAA GAC GGA AAA GCA ACA GGA AAA ACG GCA 2922
Ile Lys Val Glu Leu Tyr Gln Asp Gly Lys Ala Thr Gly Lys Thr Ala
1835 1840 1845

ACA TTA AAT GAA TCT AAT AAC TGG ACC CAT ACG TGG ACA GGA TTA GAT 2970
Thr Leu Asn Glu Ser Asn Asn Trp Thr His Thr Trp Thr Gly Leu Asp
1850 1855 1860

-continued

GAA AAA GCA AAA GGA CAA CAA GTA AAA TAC ACA GTC GAG GAA TTA ACA 3018
Glu Lys Ala Lys Gly Gln Gln Val Lys Tyr Thr Val Glu Glu Leu Thr
1865 1870 1875

AAG GTC AAA GGT TAT ACA ACA CAT GTG GAT AAC AAT GAT ATG GGT AAC 3066
Lys Val Lys Gly Tyr Thr Thr His Val Asp Asn Asn Asp Met Gly Asn
1880 1885 1890 1895

TTG ATT GTG ACG AAT AAA TAT ACG CCA GAA ACA ACA TCA ATT AGT GGT 3114
Leu Ile Val Thr Asn Lys Tyr Thr Pro Glu Thr Thr Ser Ile Ser Gly
1900 1905 1910

GAA AAA GTA TGG GAC GAC AAA GAC AAT CAA GAT GGT AAG AGA CCA GAA 3162
Glu Lys Val Trp Asp Asp Lys Asp Asn Gln Asp Gly Lys Arg Pro Glu
1915 1920 1925

AAA GTC AGT GTG AAT TTA TTG GCT GAT GGA GAG AAA GTA AAA ACG TTA 3210
Lys Val Ser Val Asn Leu Leu Ala Asp Gly Glu Lys Val Lys Thr Leu
1930 1935 1940

GAC GTG ACA TCT GAA ACA AAC TGG AAG TAC GAA TTT AAA GAC TTA CCG 3258
Asp Val Thr Ser Glu Thr Asn Trp Lys Tyr Glu Phe Lys Asp Leu Pro
1945 1950 1955

AAG TAT GAT GAA GGA AAG AAA ATA GAA TAT ACA GTG ACC GAA GAT CAC 3306
Lys Tyr Asp Glu Gly Lys Lys Ile Glu Tyr Thr Val Thr Glu Asp His
1960 1965 1970 1975

GTA AAA GAC TAC ACA ACA GAC ATC AAC GGT ACG ACA ATA ACG AAC AAG 3354
Val Lys Asp Tyr Thr Thr Asp Ile Asn Gly Thr Thr Ile Thr Asn Lys
1980 1985 1990

TAT ACA CCA GGA GAG ACA TCG GCA ACA GTA ACA AAA AAT TGG GAT GAC 3402
Tyr Thr Pro Gly Glu Thr Ser Ala Thr Val Thr Lys Asn Trp Asp Asp
1995 2000 2005

AAT AAT AAC CAA GAC GGA AAA CGA CCA ACT GAA ATC AAA GTT GAG TTA 3450
Asn Asn Asn Gln Asp Gly Lys Arg Pro Thr Glu Ile Lys Val Glu Leu
2010 2015 2020

TAT CAA GAC GGA AAA GCA ACA GGA AAA ACG GCA ACA TTA AAT GAA TCT 3498
Tyr Gln Asp Gly Lys Ala Thr Gly Lys Thr Ala Thr Leu Asn Glu Ser
2025 2030 2035

AAT AAC TGG ACC CAT ACG TGG ACA GGA TTA GAT GAA AAA GCA AAA CCA 3546
Asn Asn Trp Thr His Thr Trp Thr Gly Leu Asp Glu Lys Ala Lys Pro
2040 2045 2050 2055

CAA CAA CTA AAA TAC ACA GTC CAG GAA TTA ACA AAG GTC AAA GGT TAT 3594
Gln Gln Leu Lys Tyr Thr Val Gln Glu Leu Thr Lys Val Lys Gly Tyr
2060 2065 2070

ACA ACA CAT GTG GAT AAC AAT GAT ATG GGC AAC TTG ATT GTG ACG AAT 3642
Thr Thr His Val Asp Asn Asn Asp Met Gly Asn Leu Ile Val Thr Asn
2075 2080 2085

AAA TAT ACG CCA GAA ACA ACA TCA ATT AGC GGT GAA AAA GTA TGG GAC 3690
Lys Tyr Thr Pro Glu Thr Thr Ser Ile Ser Gly Glu Lys Val Trp Asp
2090 2095 2100

GAC AAA GAC AAT CAA GAT GGT AAG AGA CCA GAA AAA GTC AGT GTA AAT 3738
Asp Lys Asp Asn Gln Asp Gly Lys Arg Pro Glu Lys Val Ser Val Asn
2105 2110 2115

TTA TTG GCT AAC GGA GAG AAA GTA AAA ACG TTA GAC GTG ACA TCT GAA 3786
Leu Leu Ala Asn Gly Glu Lys Val Lys Thr Leu Asp Val Thr Ser Glu
2120 2125 2130 2135

ACA AAC TGG AAG TAC GAA TTT AAA GAC TTA CCG AAG TAT GAT GAA GGA 3834
Thr Asn Trp Lys Tyr Glu Phe Lys Asp Leu Pro Lys Tyr Asp Glu Gly
2140 2145 2150

AAG AAA ATA GAA TAT ACA GTG ACC GAA GAT CAC GTA AAA GAC TAC ACA 3882
Lys Lys Ile Glu Tyr Thr Val Thr Glu Asp His Val Lys Asp Tyr Thr
2155 2160 2165

ACA GAC ATC AAC GGT ACG ACA ATA ACG AAC AAG TAT ACA CCA GGA GAG 3930
Thr Asp Ile Asn Gly Thr Thr Ile Thr Asn Lys Tyr Thr Pro Gly Glu
2170 2175 2180

-continued

ACA TCG GCA ACA GTA ACA AAA AAT TGG GAT GAC AAT AAT AAC CAA GAC 3978
Thr Ser Ala Thr Val Thr Lys Asn Trp Asp Asp Asn Asn Asn Gln Asp
2185 2190 2195

GGA AAA CGA CCA ACT GAA ATC AAA GTT GAG TTA TAT CAA GAT GGA AAA 4026
Gly Lys Arg Pro Thr Glu Ile Lys Val Glu Leu Tyr Gln Asp Gly Lys
2200 2205 2210 2215

GCA ACA GGA AAA ACG GCA ATA TTA AAT GAA TCT AAT AAC TGG ACA CAT 4074
Ala Thr Gly Lys Thr Ala Ile Leu Asn Glu Ser Asn Asn Trp Thr His
2220 2225 2230

ACG TGG ACA GGA TTA GAT GAA AAA GCA AAA GGA CAA CAA GTA AAA TAC 4122
Thr Trp Thr Gly Leu Asp Glu Lys Ala Lys Gly Gln Gln Val Lys Tyr
2235 2240 2245

ACA GTC GAT GAA TTA ACA AAA GTT AAT GGC TAT ACA ACG CAT GTG GAT 4170
Thr Val Asp Glu Leu Thr Lys Val Asn Gly Tyr Thr Thr His Val Asp
2250 2255 2260

AAC AAT GAT ATG GGT AAC TTG ATT GTG ACA AAT AAA TAT ACG CCG AAA 4218
Asn Asn Asp Met Gly Asn Leu Ile Val Thr Asn Lys Tyr Thr Pro Lys
2265 2270 2275

AAA CCG AAT AAA CAA TCT ATC CTG AAA AAA CCA AAA GAC AAA ACA CCA 4266
Lys Pro Asn Lys Gln Ser Ile Leu Lys Lys Pro Lys Asp Lys Thr Pro
2280 2285 2290 2295

CCA ACT AAA CCT GAT CAT TCT AAT AAA GTT AAA CCA ACT CCC CCA GAT 4314
Pro Thr Lys Pro Asp His Ser Asn Lys Val Lys Pro Thr Pro Pro Asp
2300 2305 2310

AAG CCA TCA AAA GTG GAT AAG GAT GAT CAA CCT AAA GAT AAT AAA ACC 4362
Lys Pro Ser Lys Val Asp Lys Asp Asp Gln Pro Lys Asp Asn Lys Thr
2315 2320 2325

AAA CCT GAA AAT CCT CTA AAA GAA TTA CCA AAA ACT GGT ATG AAG ATT 4410
Lys Pro Glu Asn Pro Leu Lys Glu Leu Pro Lys Thr Gly Met Lys Ile
2330 2335 2340

ATA ACT TCA TGG ATT ACA TGG GTA TTT ATA GGT ATA TTG GGA CTG TAT 4458
Ile Thr Ser Trp Ile Thr Trp Val Phe Ile Gly Ile Leu Gly Leu Tyr
2345 2350 2355

TTA ATT TTA AGA AAA AGA TTT AAC TCA TAAACCATTA TAATTATTTT 4505
Leu Ile Leu Arg Lys Arg Phe Asn Ser
2360 2365

TATAGATAAG GCTATTCTTA GTTCTATGTA TAATACATGA TATTAATAGG TCACTTTTAA 4565

TCTGTATGTA AGCAGACTAA GAGTGGCCTT TTAAACAAAT AAAAAAA 4612